US012728164B2

(12) United States Patent
Saddow et al.

(10) Patent No.: US 12,728,164 B2
(45) Date of Patent: Sep. 8, 2026

(54) METHODS FOR TREATING CANCER USING X-RAY-INDUCED NEAR INFRARED PHOTOIMMUNOTHERAPY

(71) Applicant: UNIVERSITY OF SOUTH FLORIDA, Tampa, FL (US)

(72) Inventors: Stephen Edward Saddow, Land O Lakes, FL (US); Peter L. Choyke, Rockville, MD (US); Marco Vittorio Nardi, Levico Terme (IT); Giancarlo Salviati, Parma (IT)

(73) Assignees: University of South Florida, Tampa, FL (US); The United States of America, as Represented by the Secretary, Department of Health and Human Services, Bethesda, MD (US)

( * ) Notice: Subject to any disclaimer, the term of this patent is extended or adjusted under 35 U.S.C. 154(b) by 1056 days.

(21) Appl. No.: 17/617,652

(22) PCT Filed: Jun. 10, 2020

(86) PCT No.: PCT/US2020/036924
§ 371 (c)(1),
(2) Date: Dec. 9, 2021

(87) PCT Pub. No.: WO2020/251975
PCT Pub. Date: Dec. 17, 2020

(65) Prior Publication Data

US 2022/0241418 A1 Aug. 4, 2022

Related U.S. Application Data

(60) Provisional application No. 62/859,337, filed on Jun. 10, 2019.

(51) Int. Cl.

| | |
|---|---|
| ***A61K 41/00*** | (2020.01) |
| ***A61K 47/68*** | (2017.01) |
| ***A61K 47/69*** | (2017.01) |
| ***A61N 5/06*** | (2006.01) |
| ***A61N 5/10*** | (2006.01) |

(52) U.S. Cl.
CPC ...... *A61K 41/0057* (2013.01); *A61K 41/0038* (2013.01); *A61K 47/6851* (2017.08); *A61K 47/6929* (2017.08); *A61N 5/062* (2013.01); *A61N 5/10* (2013.01); *A61N 2005/0659* (2013.01); *A61N 2005/1098* (2013.01)

(58) Field of Classification Search
CPC . A61K 47/6851; A61K 47/6929; A61N 5/062
See application file for complete search history.

(56) References Cited

U.S. PATENT DOCUMENTS

| | | | | |
|---|---|---|---|---|
| 5,585,089 A | 12/1996 | Queen et al. | | |
| 6,960,648 B2 | 11/2005 | Bonny | | |
| 8,197,471 B1 * | 6/2012 | Tersigni | ............... | A61N 5/1001 606/27 |
| 9,488,916 B2 | 11/2016 | Bourke, Jr. et al. | | |
| 9,526,913 B2 | 12/2016 | Vo-Dinh et al. | | |
| 2002/0035243 A1 | 3/2002 | Imfeld et al. | | |
| 2002/0120100 A1 | 8/2002 | Bonny | | |
| 2003/0032594 A1 | 2/2003 | Bonny | | |
| 2003/0208249 A1 | 11/2003 | Chen | | |
| 2014/0273215 A1 * | 9/2014 | Guo | ................... | A61K 47/6923 435/375 |
| 2017/0239489 A1 | 8/2017 | Bourke, Jr. et al. | | |
| 2018/0236076 A1 * | 8/2018 | Kobayashi | ......... | A61K 41/0038 |

FOREIGN PATENT DOCUMENTS

| | | |
|---|---|---|
| WO | 2013/009475 | 1/2013 |
| WO | 2013009475 A8 | 1/2013 |

OTHER PUBLICATIONS

ICNIRP (https://www.icnirp.org/en/frequencies/infrared/index.html), accessed Mar. 7, 2025 (Year: 2025).*
Negri, M., et al. “Tuning the radial structure of core-shell silicon carbide nanowires.” CrystEngComm 17.6 (2015): 1258-1263.
Fabbri, Filippo, et al. “Carbon-doped SiO x nanowires with a large yield of white emission.” Nanotechnology 25.18 (2014): 185704.
Fabbri, Filippo, et al. “Carbon-doped SiO x nanowires with a large yield of white emission.” Nanotechnology 25.18 (2014): 185704.
Attolini, Giovanni, et al. “Growth of SiC NWs by vapor phase technique using Fe as catalyst.” Materials Letters 124 (2014): 169-172.
Fabbri F, Rossi F, Melucci M, Manet I, Attolini G, Favaretto L, Zambianchi M, Salviati G. Optical properties of hybrid T3Pyr/SiO2/3C-SiC nanowires. Nanoscale research letters. Dec. 2012;7(1):1-8.
Rossi, Francesca, et al. “Structural and luminescence properties of HfO2 nanocrystals grown by atomic layer deposition on SiC/SiO2 core/shell nanowires.” Scripta Materialia 69.10 (2013): 744-747.
Fabbri, Filippo, et al. “Enhancement of the core near-band-edge emission induced by an amorphous shell in coaxial one-dimensional nanostructure: the case of SiC/SiO2 core/shell self-organized nanowires.” Nanotechnology 21.34 (2010): 345702.
Rossi, F., et al. “Porphyrin conjugated SiC/SiOx nanowires for X-ray-excited photodynamic therapy.” Scientific reports 5.1 (2015): 1-6.
Rossi, F., et al. “Silicon carbide-based nanowires for biomedical applications.” Silicon Carbide Biotechnology. Elsevier, 2016. 311-342.
Vörös, Márton, et al. “The absorption of oxygenated silicon carbide nanoparticles.” The Journal of chemical physics 133.6 (2010): 064705.

(Continued)

*Primary Examiner* — Andrew S Rosenthal
(74) *Attorney, Agent, or Firm* — Meunier Carlin & Curfman LLC

(57) ABSTRACT

Methods for the treatment of cancers, in particular deep-tissue cancers, using x-ray induced near-infrared photoimmunotherapy are described herein.

15 Claims, 16 Drawing Sheets

(56) References Cited

OTHER PUBLICATIONS

Vörös, Márton, et al. "Publisher's Note: "The absorption spectrum of hydrogenated silicon carbide nanocrystals from ab initio calculations" [Appl. Phys. Lett. 96, 051909 (2010)]." Applied Physics Letters 96.7 (2010b): 079902.
Vörös, Marton, et al. "Influence of oxygen on the absorption of silicon carbide nanoparticles." Materials Science Forum. vol. 679. Trans Tech Publications Ltd, 2011.
Somogyi, Bálint, Viktor Zólyomi, and Adam Gali. "Near-infrared luminescent cubic silicon carbide nanocrystals for in vivo biomarker applications: an ab initio study." Nanoscale 4.24 (2012): 7720-7726.
Beke, David, et al. "Characterization of luminescent silicon carbide nanocrystals prepared by reactive bonding and subsequent wet chemical etching." Applied Physics Letters 99.21 (2011): 213108.
Beke, David, et al. "Silicon carbide quantum dots for bioimaging." Journal of Materials Research 28.2 (2013): 205-209.
Beke, David, et al. "Preparation of small silicon carbide quantum dots by wet chemical etching." Journal of Materials Research 28.1 (2013): 44-49.
Beke, David, Szekrényes, Z., et al. "Dominant luminescence is not due to quantum confinement in molecular-sized silicon carbide nanocrystals." Nanoscale 7.25 (2015): 10982-10988.
Beke, David, et al. "Identification of Luminescence Centers in Molecular-Sized Silicon Carbide Nanocrystals." The Journal of Physical Chemistry C 120.1 (2016): 685-691.
Szekrényes, Z., Beke, D., Czigány, Z., Kamarás, K., & Gali, Á. (2015). "Dominant luminescence is not due to quantum confinement in molecular-sized silicon carbide nanocrystals." Nanoscale, 7(25), 10982-10988.
Mitsunaga, Makoto, et al. "Near-infrared theranostic photoimmunotherapy (PIT): repeated exposure of light enhances the effect of immunoconjugate." Bioconjugate chemistry 23.3 (2012): 604-609.
Kobayashi, Hisataka, and Peter L. Choyke. "Super enhanced permeability and retention (SUPR) effects in tumors following near infrared photoimmunotherapy." Nanoscale 8.25 (2016): 12504-12509. Epub Oct. 7, 2015.
Sano, Kohei, et al. "Markedly enhanced permeability and retention effects induced by photo-immunotherapy of tumors." ACS nano 7.1 (2013): 717-724.
Kobayashi, Hisataka, et al. "Super-enhanced permeability and retention (SUPR) effect induced by photo-immunotherapy (PIT) can accommodate massive nano- sized reagents deep into tumors." (2013): 4512-4512.
Nakajima, Takahito, et al. "The effects of conjugate and light dose on photo-immunotherapy induced cytotoxicity." BMC cancer 14.1 (2014): 1-7.
Bigi, Franca, et al. "Silica-bound decatungstates as heterogeneous catalysts for H2O2 activation in selective sulfide oxidation." Journal of Catalysis 250.2 (2007): 222-230.
Ikeda, M., and H. Matsunami. "Free exciton luminescence in 3C, 4H, 6H, and 15R SiC." physica status solidi (a) 58.2 (1980): 657-663.
Steuer, Heiko, Rumen Krastev, and Nicolas Lembert. "Metallic oxide nanoparticles stimulate blood coagulation independent of their surface charge." Journal of Biomedical Materials Research Part B: Applied Biomaterials 102.5 (2014): 897-902.
Saddow, et al. "Enabling NIR-PIT therapy to treat deep-tissue cancer". NIH; University of South Florida. 2020. grantome.com/grant/NIH/R21-CA223969-02.
International Search Report and Written Opinion in PCT/US2020/036924. Mailed Sep. 4, 2020. 9 pages.

* cited by examiner

METHODS FOR TREATING CANCER USING X-RAY-INDUCED NEAR INFRARED PHOTOIMMUNOTHERAPY

CROSS REFERENCE TO RELATED APPLICATIONS

This application is a United States National Phase Patent Application of International Patent Application Number PCT/US2020/036924, filed on Jun. 10, 2020, which claims the benefit of priority to U.S. Provisional Application No. 62/859,337, filed Jun. 10, 2019, which is incorporated by reference herein in its entirety.

STATEMENT REGARDING FEDERALLY SPONSORED RESEARCH

This invention was made with government support under Grant No. 1R21CA223969-01A1 awarded by the National Institutes of Health. The government has certain rights in the invention.

FIELD

The present disclosure is directed to methods for treating cancers using near-infrared photoimmunotherapy induced by x-ray irradiation, in particular deep-tissue cancers.

BACKGROUND

Current cancer treatment methods strive to balance the killing of cancer cells while avoiding adverse effects on healthy tissue. Dose-limiting toxicity provides significant challenges to the use and effectiveness of conventional cancer treatments such as chemotherapy. While several treatments are being explored that target killing of cancer cells while sparing normal cells, no such therapies haven been developed for locally advanced, deep visceral cancers.

Near-Infrared Photoimmunotherapy (NIR-PIT) is a targeted therapy for cancer that combines the use of an antibody-photoabsorber conjugate (APC) with low energy near-infrared light therapy to selectively kill cancer cells with improved selectivity. The antibody component of the APC is typically chosen for optimal binding to a particular cancer based on its cell surface expression of a tumor antigen (for example, EGFR, HER2, or PSMA). IR700 is typically used as the photoabsorber in the APC due to its hydrophobicity, making the photoabsorber only toxic to cells when bound to the cell membrane via the APC. When the tumor is exposed to near-infrared light (approximately 690 nm), rapid cell necrosis occurs due to changes in cell membrane permeability. However, no damage is observed in normal adjacent cells due to minimal expression of the targeted tumor antigen. NIR-PIT is currently being studied in clinical trials for the treatment of inoperable recurrent head and neck cancers using the antibody-photoabsorber conjugate Cetuximab-IR700.

In order for a tumor cell to be irreversibly damaged by NIR-PIT, at least approximately 10,000 copies of the antigen need to be expressed on the targeted cell. Because the APC does not initially distribute evenly throughout the tumor, repeated near-infrared light exposures are needed to allow for redistribution after each treatment. Additionally, near-infrared light does not penetrate deep enough to treat deep visceral tumors, either putting these tumors out of range for repeated light exposures or requiring surgical implantation of a fiber optic light or endoscopy to reach deep-tissue cancer cells. Thus, invasive interventions would be necessarily repeated to provide the necessary repeated NIR light exposures for effective therapy.

Thus, there is a clear need for the development of NIR-PIT methods that can be used with cancers, in particular deep-tissue cancers, without the requirement of multiple surgical interventions to introduce the NIR light.

SUMMARY

The present disclosure provides methods for treating cancers using near-infrared photoimmunotherapy (NIR-PIT) by additionally using x-ray absorbing nanostructures (NSs) that emit NIR light within the tumor upon x-ray irradiation. The methods described herein allow treatment of cancers, in particular deep-tissue cancers, that would otherwise not be effectively treated by current NIR-PIT methods due to the poor penetration of NIR through the skin of the patient, or that otherwise would require surgical or endoscopic intervention during each repeated NIR-PIT treatment.

According to the present methods, a subject with cancer is first administered a near-infrared antibody-photoabsorber conjugate (APC) which is selectively taken up by the cancer. In some instances, the cancer is then exposed to NIR light either through partial exposure by irradiation through the skin or by introduction of a fiber optic light in the tumor either surgically or endoscopically. Exposure of the cancer containing the APC to NIR leads to cell necrosis along with increased deposition of macromolecules in the cancer, an effect called Super Enhanced Permeability and Retention (SUPR). The SUPR effect allows for selective and ready uptake of x-ray absorbing nanostructures (NSs) into the tumor upon their subsequent administration. The x-ray absorbing NSs can be administered and selectively taken up into the tumor without the SUPR effect. These x-ray absorbing NSs will emit NIR light locally in the tumor when exposed to x-ray radiation, activating or reactivating the APCs and leading to further cell necrosis. Due to the ability of x-ray radiation to more deeply penetrate tissues than NIR light, this allows for multiple instances of activation of the APCs within the cancer without potentially requiring surgical interventions each time to introduce NIR light, such as would be necessary with certain cancers such as deep-tissue cancers.

Thus, a method is provided for the treatment of a cancer in a subject in need thereof comprising:

(a) administering a therapeutically effective amount of a near-infrared antibody-photoabsorber conjugate (APC) to the subject, wherein upon administration the APC is at least partially taken up into the cancer tissue and binds to a cell surface protein present within the cancer tissue;

(b) optionally exposing the cancer tissue to near-infrared (NIR) light;

(c) administering a therapeutically effective amount of an x-ray absorbing nanostructure (NS) to the subject, wherein the x-ray absorbing NS is at least partially taken up into the cancer tissue upon administration;

(d) exposing the cancer tissue to x-ray radiation, wherein upon exposure of the cancer tissue to x-ray radiation, the x-ray absorbing NS absorbs the x-ray radiation and emits NIR light; and optionally repeating steps (c) and (d) one or more times.

The x-ray absorbing nanostructures (NSs) as described herein can be selected from any biocompatible nanostructures that absorb x-ray radiation and subsequently emit near-infrared (NIR) light. In some embodiments, the x-ray absorbing nanostructure emits light having a wavelength of about 660 nm to about 710 nm, such as about 680 to 700 nm, such that the emission is subsequently absorbed by the APCs bound to the cancer tissue. In some embodiments, the x-ray absorbing NSs include silicon carbide (SiC), silicon dioxide ($SiO_2$), hydroxyapatite, zinc-gallium-oxide (ZGO), or a combination thereof. The X-ray absorbing NS can further comprise a dopant such as europium (Eu), chromium III ($Cr^{3+}$), gold (Au), other x-ray absorbing heavy element (or heavy metal) dopants, or a combination thereof. The dopant can be present in an amount of 10% or less by weight, from 0.01 to 10% by weight, or from 0.05 to 5% by weight, based on the total weight of the X-ray absorbing nanostructure. The nanostructure can be in the form of a nanoparticle or a nanowire, including for example, core/shell nanowires or core/shell nanoparticles. For example, the x-ray absorbing NSs can include a europium-doped $SiO_2$ nanoparticle (Eu—$SiO_2$), europium-doped hydroxyapatite nanoparticle (Eu—HA), $Cr^{3+}$ doped zinc-gallium-oxide nanoparticle (ZGO:Cr), $Cr^{3+}$ doped zinc-gallium-oxide with SiC core nanoparticle (ZGO:Cr_SiC), SiC nanowire, SiC nanoparticle, or combinations thereof.

The x-ray absorbing NS can have a diameter of less than about 350 nm, such as from about 1 nm to about 350 nm, from about 50 nm to about 350 nm, from about 100 nm to about 350 nm, 100 nm or less, from about 1 nm to about 100 nm, from about 10 nm to about 50 nm. The x-ray absorbing NS can be functionalized with a surface-bound molecule. Such surface bound molecules can be selected from a surfactant, a dispersant, a targeting agent which facilitates delivery of the nanoparticle to the cancer cell, or a combination thereof.

The antibody-photoabsorber conjugate (APCs) as used in the methods described herein is composed of an antibody that binds to a cell surface protein of the targeted cancer conjugated to a photoabsorber. In some embodiments, the antibody-photoabsorber conjugate (APC) as used herein comprises an antibody-IR700 conjugate. The antibody component of the APC as used herein can be any antibody that selectively binds to a tumor antigen that is expressed on the cell surface of the cancer to be treated. Representative examples of such tumor antigens include, but are not limited to, epidermal growth factor receptor (EGFR), human epidermal growth factor receptor 2 (HER2), or prostate specific membrane antigen (PSMA). In some embodiments, the APC comprises an EGFR antibody-IR700 conjugate. In some embodiments, the APC comprises a cetuximab-IR700 conjugate. In other embodiments, the APC comprises a panitumumab-IR700 conjugate.

Also disclosed herein are kits that contain the APC and the x-ray absorbing NS as used in the methods described herein.

The foregoing and other features of the disclosure will become apparent from the following detailed description of several embodiments which proceed with reference to the accompanying drawings.

BRIEF DESCRIPTION OF THE DRAWINGS

FIG. 10A shows an x-ray Spectra (Bright XEOL detected @21 keV (Elettra) but non-penetrating x-rays used) conducted on a Bruker XRF M1 Tool. FIG. 10B shows a 50 kVp Bremsstrahlung calculated spectra without and with 2.5 cm of water which approximates human tissue x-ray absorption. FIG. 10C shows an XEOL from ZnS without and with the insertion of a 2.5 cm piece of beef to simulate human tissue. Note XEOL was observed with an approximately 5× reduction as predicted in the calculation of FIG. 10B.

DETAILED DESCRIPTION

Figure 1:
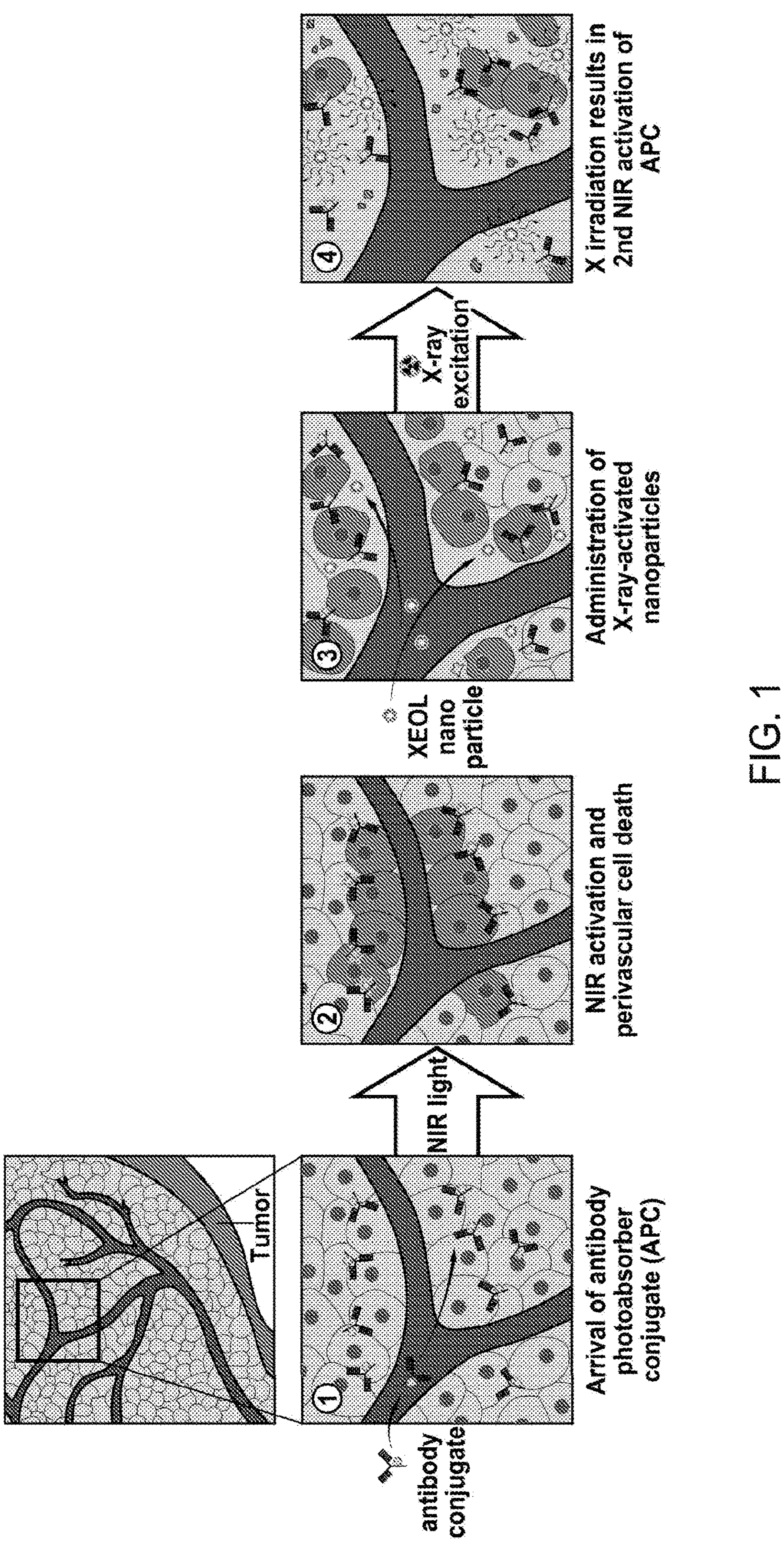
FIG. 1 is a scheme that shows the effects of x-ray induced near-infrared photoimmunotherapy. Panels 1 and 2 show the super-enhanced permeability and retention (SUPR) effect after NIR-PIT. Panel 1 shows the arrival of the antibody-photoabsorber conjugate (APC) with preferential binding to tumor cells surrounding the vessels. Panel 2 shows activation with NIR light and subsequent perivascular cell death. Panel 3 shows how after exposure to NIR light, the perivascular spaces are opened, allowing for extravasation of x-ray absorbing nanostructures (NSs) deeper into the tumor. Panel 4 shows how x-ray excitation induces NIR emission for the x-ray absorbing NSs to kill deep-tissue cancer cells.
Figure 2:
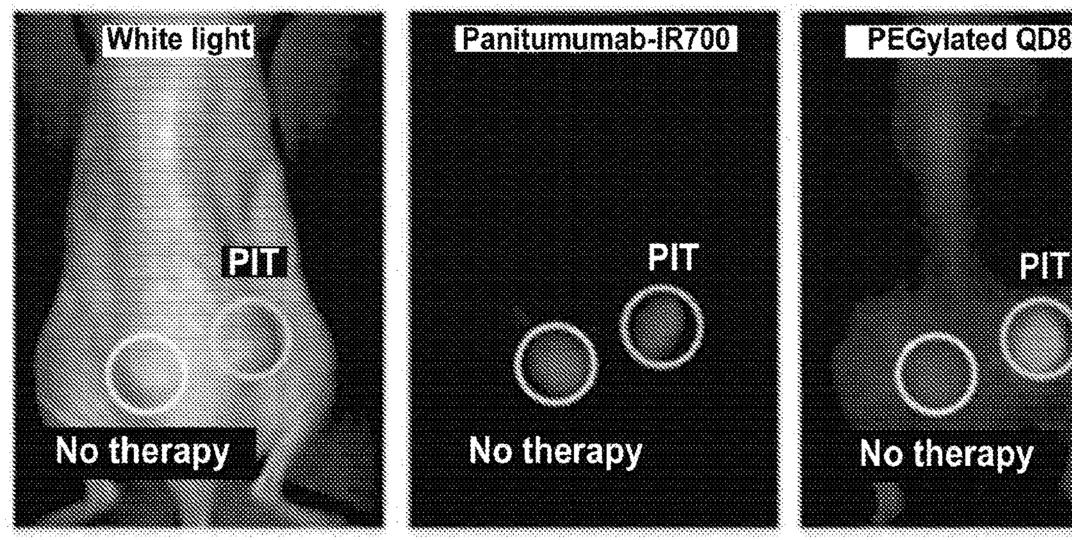
FIG. 2 shows images of a mouse with two implanted A431 tumors. Prior to NIR-PIT, equal fluorescence can be seen in the control tumor and the targeted tumor as shown in the second panel from IR700 fluorescence due to conventional tumor enhanced permeability and retention. As shown in the third panel, NIR-PIT treated tumors preferentially receive pegylated QDot800 (approximately 20 nm in diameter) with 24-fold greater light emission than controls.

The following description of the disclosure is provided as an enable teaching of the disclosure in its best, currently known embodiments. To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are part of the present disclosure. Thus, the following description is provided as illustrative of the principles of the present disclosure and not in limitation thereof.

Definitions

Unless defined otherwise, all technical and scientific terms used herein have the same meaning as commonly understood to one of ordinary skill in the art to which this invention belongs. The following definitions are provided for the full understanding of terms used in the specification.

As used in the specification and claims, the singular form “a”, “an”, and “the” include plural references unless the context clearly dictates otherwise. For example, the term “an agent” includes a plurality of agents, including mixtures thereof.

As used herein, the terms “may,” “optionally,” and “may optionally” are used interchangeably and are meant to include cases in which the condition occurs as well as cases in which the condition does not occur. Thus, for example, the statement that a formulation “may include an excipient” is meant to include cases in which the formulation includes an excipient as well as cases in which the formulation does not include an excipient.

Administration” to a subject includes any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra- articular, intra-synovial, intrasternal, intrathecal, intraperitoneal, intrahepatic, intralesional, and intracranial injections or infusion techniques), and the like. “Concurrent administration”, “administration in combination”, “simultaneous administration” or “administered simultaneously” as used herein, means that the compounds are administered at the same point in time or essentially immediately following one another. In the latter case, the two compounds are administered at times sufficiently close that the results observed are indistinguishable from those achieved when the compounds are administered at the same point in time. “Systemic administration” refers to the introducing or delivering to a subject an agent via a route which introduces or delivers the agent to extensive areas of the subject’s body (e.g. greater than 50% of the body), for example through entrance into the circulatory or lymph systems. By contrast, “local administration” refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration but are undetectable or detectable at negligible amounts in distal parts of the subject’s body. Administration includes self-administration and the administration by another.

“Antibody” can refer to a polypeptide ligand comprising at least a light chain or heavy chain immunoglobulin variable region which specifically recognizes and binds an epitope of an antigen, such as a tumor-specific protein. Antibodies are composed of a heavy chain and a light chain, each of which has a variable region, termed the variable heavy ($V_H$) region and the variable light ($V_L$) region. Together, the $V_H$ region and the $V_L$ region are responsible for binding the antigen recognized by the antibody. Antibodies include intact immunoglobulins and the variants and portion of antibodies well known in the art, such as Fab fragments, Fab' fragments, $F(ab)'_2$ fragments, single chain Fv proteins (“scFv”), and disulfide stabilized Fv proteins (“DsFv”). A scFv protein is a fusion protein in which a light chain variable region of an immunoglobulin and a heavy chain variable region of an immunoglobulin are bound by a linker, while in dsFvs, the chains have been mutated to introduce a disulfide bond to stability the association of the chains. The term also includes genetically engineered forms such as chimeric antibodies (for example, humanized murine antibodies) and heteroconjugate antibodies (such as bispecific antibodies). See also, *Pierce Catalog and Handbook,* 1994-1995 (Pierce Chemical Co., Rockford Ill.); Kuby, J. *Immunology,* 3rd Ed., W. H. Freeman & Co., New York, 1997. Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA, and IgE. Each heavy and light chain contains a constant region and a variable region (also known as “domains”). In combination, the heavy and the light chain variable regions specifically bind the antigen. Light and heavy chain variable regions contain a “framework” region interrupted by three hypervariable also called “complementarity-determining regions” or “CDRs”. The extent of the framework region and CDRs have been defined (see Kabat et al., *Sequences of Proteins of Immunological Interest*, U.S. Department of Health and Human Services, 1991). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space. The CDRs are primarily responsible for binding to an epitope of an antigen. The CDRs of each chain are typically referred to as CDR1, CDR2, and CDR3, numbered sequentially starting from the N-terminus, and also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are call specificity determining residues (SDRs). References to "$V_H$" or "VH" refer to the variable region of an immunoglobulin heavy chain, including that of an Fv, scFv, dsFv, or Fab. References to "$V_L$" or "VL" refer to the variable region of an immunoglobulin light chain, including that of an Fv, scFv, dsFv, or Fab. A "monoclonal" antibody is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies. A "chimeric antibody" has framework residues from one species, such as a human, and CDRs (which generally confer antigen binding) from another species, such as a murine antibody that specifically binds mesothelin. A "humanized" immunoglobulin is an immunoglobulin including a human framework region and one or more CDRs from a non-human (for example a mouse, rat, or synthetic) immunoglobulin. The non-human immunoglobulin providing CDRs is termed a "donor", and the human immunoglobulin providing the framework is termed an "acceptor". In one embodiment, all the CDRs are form the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody can have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089). A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. All parts of a human immunoglobulin are substantially identical to corresponding parts of natural human immunoglobulin sequences.

"Specifically binds" refers to the ability of individual antibodies to specifically immunoreact with an antigen, such as a tumor-specific antigen, relative to binding to unrelated proteins, such as non-tumor proteins, from example β-actin. For example, a HER2-specific binding agent binds substantially only the HER2 protein in vitro or in vivo. As used herein, the term "tumor-specific binding agent" includes tumor-specific antibodies and other agents that bind substantially only to a tumor-specific protein in that preparations. The binding is a non-random binding reaction between an antibody molecule and an antigenic determinant of the T cell surface molecule. The desired binding specificity is typically determined from the reference point of the ability of the antibody to differentially bind the T cell surface molecule and an unrelated antigen, and therefore distinguish between two different antigens, particularly when the two antigens have unique epitopes. An antibody that specifically binds to a particular epitopes is referred to as a "specific antibody". In some examples, an antibody specifically binds to a target (such as a cell surface protein) with a binding constant that is at least $10^3$ $M^{-1}$ greater, $10^4$ $M^{-1}$ greater or $10^5$ $M^{-1}$ greater than a binding constant for other molecules in a sample or subject. In some examples, an antibody (e.g. a monoclonal antibody) or fragments thereof, has an equilibrium constant (Kd) of 1 nM or less. For example, an antibody binds to a target, such as tumor-specific protein with a binding affinity of at least about $0.1\times10^{-8}$ M, at least about $0.3\times10^{-8}$ M, at least about $0.5\times10^{-8}$ M, at least about $0.75\times10^{-8}$ M, at least about $1.0\times10^{-8}$ M, at least about $1.3\times10^{-8}$ M, at least about $1.5\times10^{-8}$ M, or at least about $2.0\times10^{-8}$ M. Kd values, for example, can be determined by competitive ELISA (enzyme-linked immunosorbent assay) or using a surface-plasmon resonance device such as the Biacore T100, which is available from Biacore, Inc., Piscataway, N.J.

An "antigen" can refer to a compound, composition, or substance that can stimulate the production of antibodies or a T cell response in an animal, including compositions (such as one that includes a tumor-specific protein) that are injected or absorbed into an animal. An antigen reacts with the products of specific humoral or cellular immunity, including those induced by heterologous antigens, such as the disclosed antigens. "Epitope" or "antigen determinant" refers to the region of an antigen to which B and/or T cells respond. In one embodiment, T cells respond to the epitope, when the epitope is presented in conjunction with an MHC molecule. Epitopes can be formed from both contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitopes typically includes at least 3, and more usually, at least 5, about 9, or about 8-10 amino acids in a unique spatial conformation. Methods of determining spatial conformation of epitopes include, for example, x-ray crystallography and nuclear magnetic resonance. Examples of antigens include, but are not limited to, peptides, lipids, polysaccharides, and nucleic acids containing antigenic determinants, such as those recognized by an immune cell. In some examples, an antigen includes a tumor-specific peptide (such as one found on the surface of a cancer cell) or immunogenic fragment thereof.

"Pharmaceutically acceptable" component can refer to a component that is not biologically or otherwise undesirable, e.g., the component can be incorporated into a pharmaceutical formulation and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Photoimmunotherapy" (PIT) refers to molecular targeted therapeutics that utilize a target specific photosensitizer (also referred to as a photoabsorber) conjugated to monoclonal antibodies (mAb) targeting cell surface receptors. In some embodiments, the photosensitizer used is a near infrared (NIR) phthalocyanine dye, for example IR700. In one example, the cell surface receptor is one found specifically on cancer cells, such as HER1, HER2 or PSMA, and thus PIT can be used to kill such cells. Cell death of the cells occurs when the antibody-photoabsorber conjugate molecule binds to the cells and the cells are irradiated, for example with near-infrared light, while cells that do not express the cell surface receptor recognized by the antibody-photoabsorber conjugate are not killed in significant numbers.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., rheumatoid arthritis). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the control of chronic inflammation. Therapeutically effective amounts of a given therapeutic agent will typically vary with respect to factors such as the type and severity of the disorder or disease being treated and the age, gender, weight, and general condition of the subject. Thus, it is not always possible to specify a quantified "therapeutically effective amount." However, an appropriate "therapeutically effective amount" in any subject case can be determined by one of ordinary skill in the art using routine experimentation. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. It is understood that, unless specifically stated otherwise, a "therapeutically effective amount" of a therapeutic agent can also refer to an amount that is a prophylactically effective amount. In some instances, a desired biological or medical response is achieved following administration of multiple dosages of the composition to the subject over a period of days, weeks, or years.

"Treat," "treating," "treatment," and grammatical variations thereof as used herein, include the administration of a composition with the intent or purpose of partially or completely, delaying, curing, healing, alleviating, relieving, altering, remedying, ameliorating, improving, stabilizing, mitigating, and/or reducing the intensity or frequency of one or more a diseases or conditions, a symptom of a disease or condition, or an underlying cause of a disease or condition. Treatments can be applied, prophylactically, palliatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for day(s) to years prior to the manifestation of symptoms of an infection.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

Antibody-Photoabsorber Conjugates (APCs)

The antibody-photoabsorber conjugate (APCs) as used in the methods described herein is composed of an antibody that binds to a cell surface protein of the targeted cancer conjugated to a photoabsorber. In some embodiments, the antibody-photoabsorber conjugate is composed on an antibody as described herein conjugate to more than one photoabsorber molecule, for example two, three, four, five, or more photoabsorber molecules.

The photoabsorber as used in the APCs described herein can be any molecule that is capable of absorbing near-infrared light of a wavelength of about 660 nm or greater, about 680 nm or greater, about 700 nm or greater, about 710 nm or greater, about 710 nm or greater, about 730 nm or greater, about 750 nm or greater, about 770 nm or greater, about 780 nm or greater, or about 800 nm or greater. In some embodiments, the photoabsorber absorbs NIR light of a wavelength of about 660 nm to about 1,000 nm, of about 660 nm to about 800 nm, of about 660 nm to about 710 nm, of about 660 nm to about 700 nm, of about 670 nm to about 700 nm, of about 670 nm to about 710 nm, of about 680 nm to 710 nm, of about 690 nm to 710 nm, of about 670 nm to about 690 nm, of about 700 nm, or of about 680 nm. In preferred embodiments, the photoabsorber is IR700 (also known as IRDye™ 700DX) having the following formula:

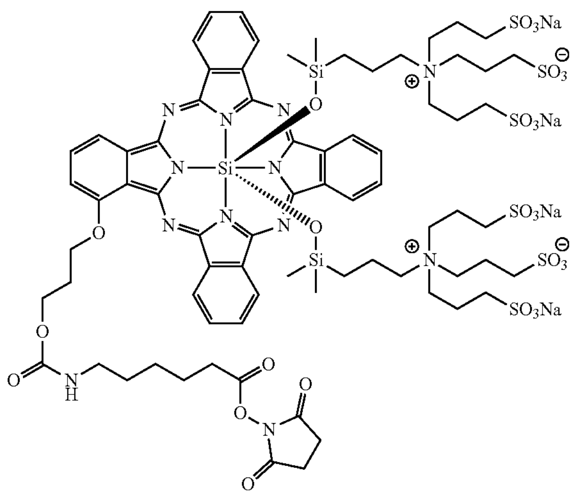

IR700 is commercially available from LI-COR (Lincoln, Nebr.). IR700 has several favorable chemical properties for its use in the APCs described herein. IR700 is a relatively hydrophilic dye and can be covalently conjugated with an antibody via reaction of the N-hydroxysuccinimide ester groups with any amino groups present on the antibody. IR700 has an extinction coefficient of about $2.1\times10^5$ $M^{-1}$ $cm^{-1}$ at the absorption maximum of 689 nm. Photosensitizers such as the hematoporphyrin derivative Photofrin ($1.2\times10^3$ $M^{-1}$ $cm^{-1}$ at 630 nm), meta-tetrahydroxyphenylchlorin Foscan™ ($2.2\times10^4$ $M^{-1}$ $cm^{-1}$ at 652 nm), and mono-L-aspartylchlorin e6 NPe6/Laserphyrin™ ($4.0\times10^4$ $M^{-1}$ $cm^{-1}$ at 654 nm) may also be used in the antibody-photoabsorber conjugate.

In some embodiments, the antibody-photoabsorber conjugate is one described in WO2013/009475, which is incorporated by reference herein for its teachings of antibody-photoabsorber conjugates.

As described herein, the antibody-photoabsorber conjugate comprises an antibody that binds to a cell surface protein of the targeted cancer. In one example, the protein on the cell surface of the target cancer cell to be killed is not present in significant amounts on other cells, such as healthy cells in a human subject. For example, the cell surface protein can be a receptor that is only found on the target cell type.

In one specific example, the cell surface protein is a tumor-specific protein (also known in the art as a tumor-specific antigen), such as members of the EGF receptor family (for example but not limited to HER1, HER2, HERS, or HER4) and cytokine receptors (for example but not limited to CD20, CD25, IL-13R, CDS, or CD52). Tumor-specific proteins are those proteins that are unique to cancer cells or are much more abundant on them, as compared to other cells, such as normal cells. For example, HER2 is primarily found in breast cancers, while HER1 is primarily found in adenocarcinomas, which can be found in many organs such as the pancreas, breast, prostate and colon.

Representative tumor-specific proteins that can be found on a target cancer cell (and to which an antibody specific for that protein can be used to formulate an antibody-photoabsorber conjugate molecule) include but are not limited to: any of the various MAGES (Melanoma-Associated Antigen E) including MAGE1, MAGE2, MAGE3, MAGE4; any of the various tyrosinates; mutant ras; mutant p53; p97 melanoma antigen; human milk fat globule (HMFG) associated with breast tumors; any of the various BAGEs (Human B Melanoma-Associated Antigen E), including BAGE1 and BAGE2; any of the various GAGES (G antigen), including GAGE1 or any of GAGE2-GAGE6; various gangliosides, and CD25.

Other tumor-specific antigens include: the HPV 16/18 and E6/E7 antigens associated with cervical cancers; mucin (MUC 1)-KLH antigen associated with breast carcinoma; CEA (carcinoembryonic antigen) associated with colorectal cancer; gp100 associated with for example melanoma; MART1 antigens associated with melanoma; cancer antigen 125 (CA125, also known as mucin 16 or MUC16) associated with ovarian or other cancers; alpha-fetoprotein (AFP) associated with liver cancer; Lewis Y antigen associated with colorectal, biliary, breast, small-cell lung, and other cancers; tumor-associated glycoprotein 72 (TAG72) associated with adenocarcinomas; and the PSA antigen associated with prostate cancer.

Other exemplary tumor-specific proteins further include, but are not limited to: PMSA (prostate membrane specific antigen) associated with solid tumor neovasculature as well as prostate cancer; HER-2 (human epidermal growth factor receptor 2) associated with breast cancer, ovarian cancer, stomach cancer and uterine cancer; HER-1 associated with lung cancer, anal cancer, and glioblastoma as well as adenocarcinomas; NY-ESO-1 associated with melanomas, sarcomas, testicular carcinomas, and other cancers; hTERT (aka telomerase); proteinase 3; and Wilms tumor 1 (WT-1). In one example, the tumor-specific protein is CD52) associated with chronic lymphocytic leukemia; CD33 associated with myelogenous leukemia; and CD20 associated with non-Hodgkin lymphoma.

A person of skill in the art will recognize that because cell surface protein sequences are publicly available, that making or purchasing antibodies specific for such proteins is routine. For example, if the tumor-specific protein HER2 is selected as a target, antibodies specific for HR2 (such as trastuzumab) can be purchased or generated attached to an appropriate photoabsorber, for example the IR700 dye. In one example, a patient is treated with at least two different antibody-photoabsorber conjugate molecules. In one example, the two different antibody-photoabsorber conjugate molecules are specific for the same protein (such as HER-2) but are specific for different epitopes of the protein (such as epitope 1 and epitope 2 of HER-2). In another example, the two different antibody-photoabsorber conjugate molecules are specific for two different proteins or antigens, such as one antibody specific for CD4, and another antibody specific for CD25, which could be used for example to a treat a T cell leukemia. For example, anti-HER1-IR700 and antiHER2-IR700 could be injected together as a cocktail to facilitate killing of cell bearing either HER1 or HER2. In one example, the antibody is a humanized monoclonal antibody. Antibody-IR700 conjugate molecules can be generated using routine methods, for example by those described in WO2013/009475, which is incorporated by reference herein for its teachings of antibody-photoabsorber conjugates.

In some embodiments, the tumor-specific protein is HER1. In some embodiments, the antibody-photoabsorber conjugate is a cetuximab-photoabsorber conjugate. In some embodiments, the antibody-photoabsorber conjugate is a cetixumab-IR700 conjugate. In some embodiments, the antibody-photoabsorber conjugate is a panitumamab-photoabsorber conjugate. In some embodiments, the antibody-photoabsorber conjugate is a panitumamab-IR700 conjugate. In some embodiments, the antibody-photoabsorber conjugate is a zalutumumab-photoabsorber conjugate. In some embodiments, the antibody-photoabsorber conjugate is a zalutumumab-photoabsorber conjugate. In some embodiments, the antibody-photoabsorber conjugate is a nimotuzumab-photoabsorber conjugate. In some embodiments, the antibody-photoabsorber conjugate is a nimotuzumab-IR700 conjugate. In some embodiments, the antibody-photoabsorber conjugate is a matuzumab-photoabsorber conjugate. In some embodiments, the antibody-photoabsorber conjugate is a matuzumab-IR700 conjugate.

In some embodiments, the tumor-specific protein is HER2. In some embodiments, the antibody-photoabsorber conjugate is a trastuzumab-photoabsorber conjugate. In some embodiments, the antibody-photoabsorber conjugate is a trastuzumab-IR700 conjugate. In some embodiments, the antibody-photoabsorber conjugate is a pertuzumab-photoabsorber conjugate. In some embodiments, the antibody-photoabsorber conjugate is a pertuzumab-IR700 conjugate.

In some embodiments, the tumor-specific protein is CD20. In some embodiments, the antibody-photoabsorber conjugate is a tositumomab-photoabsorber conjugate. In some embodiments, the antibody-photoabsorber conjugate is a tositumomab-IR700 conjugate. In some embodiments, the antibody-photoabsorber conjugate is a rituximab-photoabsorber conjugate. In some embodiments, the antibody-photoabsorber conjugate is a rituximab-IR700 conjugate. In some embodiments, the antibody-photoabsorber conjugate is an ibritumomab-photoabsorber conjugate. In some embodiments, the antibody-photoabsorber conjugate is an ibritumomab-IR700 conjugate.

In some embodiments, the tumor-specific protein is CD25. In some embodiments, the antibody-photoabsorber conjugate is a daclizumab-photoabsorber conjugate. In some embodiments, the antibody-photoabsorber conjugate is a daclizumab-photoabsorber conjugate.

In some embodiments, the tumor-specific protein is CD33. In some embodiments, the antibody-photoabsorber conjugate is a gemtuzumab-photoabsorber conjugate. In some embodiments, the antibody-photoabsorber conjugate is a gemtuzumab-IR700 conjugate.

In some embodiments, the tumor-specific protein is CD52. In some embodiments, the antibody-photoabsorber conjugate is an alemtuzumab-photoabsorber conjugate. In some embodiments, the antibody-photoabsorber conjugate is an alemtuzumab-IR700 conjugate.

In some embodiments, the tumor-specific protein is CEA. In some embodiments, the antibody-photoabsorber conjugate is a CEA-scan-photoabsorber conjugate. In some embodiments, the antibody-photoabsorber conjugate is a CEA-scan-IR700 conjugate. In some embodiments, the antibody-photoabsorber conjugate is a colo101-photoabsorber conjugate. In some embodiments, the antibody-photoabsorber conjugate is a colo101-photoabsorber conjugate.

In some embodiments, the tumor specific protein is CA125. In some embodiments, the antibody-photoabsorber conjugate is an OC125-photoabsorber conjugate. In some embodiments, the antibody-photoabsorber conjugate is an OC125-IR700 conjugate.

In some embodiments, the tumor-specific protein is AFP. In some embodiments, the antibody-photoabsorber conjugate is an ab75705-photoabsorber conjugate. In some embodiments, the antibody-photoabsorber conjugate is an ab75705-IR700 conjugate.

In some embodiments, the tumor-specific protein is Lewis Y. In some embodiments, the antibody-photoabsorber conjugate is a B3-photoabsorber conjugate. In some embodiments, the antibody-photoabsorber conjugate is a B3-IR700 conjugate.

In some embodiments, the tumor-specific protein is TAG72. In some embodiments, the antibody-photoabsorber conjugate is a B72.3-photoabsorber conjugate. In some embodiments, the antibody-photoabsorber conjugate is a B672.3-IR700 conjugate.

In some embodiments, the tumor-specific protein is VEGF. In some embodiments, the antibody-photoabsorber conjugate is a bevacizumab-photoabsorber conjugate. In some embodiments, the antibody-photoabsorber conjugate is a bevacizumab-IR700 conjugate. In some embodiments, the antibody-photoabsorber conjugate is a ramucirumab-photoabsorber conjugate. In some embodiments, the antibody-photoabsorber conjugate is a ramucirumab-IR700 conjugate. In some embodiments, the antibody-photoabsorber conjugate is a ranibizumab-photoabsorber conjugate. In some embodiments, the antibody-photoabsorber conjugate is a ranibizumab-IR700 conjugate.

In some embodiments, the tumor-specific protein is PSMA. In some embodiments, the antibody-photoabsorber conjugate is a capromab-photoabsorber conjugate. In some embodiments, the antibody-photoabsorber conjugate is a capromab-IR700 conjugate.

In some embodiments, the tumor-specific protein is EGFR. In some embodiments, the antibody-photoabsorber conjugate is a necitumumab-photoabsorber conjugate. In some embodiments, the antibody-photoabsorber conjugate is a necitumumab-IR700 conjugate.

In some embodiments, the tumor-specific protein is PDGFRα. In some embodiments, the antibody-photoabsorber conjugate is an olaratumab-photoabsorber conjugate. In some embodiments, the antibody-photoabsorber conjugate is an olaratumab-IR700 conjugate.

The tumor contacted with the antibody-photoabsorber conjugate is irradiated as in step (b) of the methods described herein with near-infrared light, for example light having a wavelength of about 660 nm to about 710 nm. In some embodiments, the tumor contacted antibody-photoabsorber conjugate is irradiated with light having a wavelength of about 660 nm to about 700 nm, of about 680 nm to about 700 nm, or of about 670 nm to about 690 nm. In some preferred embodiments, the tumor contacted with the APC is irradiated with light having a wavelength of about 680 nm. In some embodiments, the tumor contacted with the APC is irradiated at a dose of at least 1 J $cm^{-2}$, at least 10 J $cm^{-2}$, at least 30 J $cm^{-2}$, at least 50 J $cm^{-2}$, at least 100 J $cm^{-2}$, or at least 500 J $cm^{-2}$, for example 1-1000 J $cm^{-2}$, 1-500 J $cm^{-2}$, 30 to 50 J $cm^{-2}$, 10-100 J $cm^{-2}$, or 10-50 J $cm^{-2}$.

The tumor contacted with the antibody-photoabsorber conjugate can be irradiated in step (b) with any suitable source of near-infrared light as would be found suitable for the intended purpose. In some embodiments, the source can be a chamber into which the patient is inserted that emits NIR light. In other embodiments, the source can be a NIR led that can be placed on the site of the tumor. In some embodiments, particularly those involving deep-tissue tumors, the source might be attached to laparoscopic equipment or other surgical equipment to insert the NIR light source either in or around the site of the tumor. In some embodiments, the source can be luminescence from the x-ray absorbing nanostructures as further discussed herein.

X-Ray Absorbing Nanostructures (NSs)

The x-ray absorbing nanostructures (NSs) as used herein can be selected from any biocompatible nanostructures that absorb x-ray radiation and subsequently emit near-infrared (NIR) light. In some embodiments, the x-ray absorbing NSs emit NIR light at a wavelength of about 660 nm or greater, about 680 nm or greater, about 700 nm or greater, about 710 nm or greater, about 710 nm or greater, about 730 nm or greater, about 750 nm or greater, about 770 nm or greater, about 780 nm or greater, or about 800 nm or greater. In some embodiments, the x-ray absorbing NSs emit NIR light at a wavelength from about 660 nm to about 1,000 nm, of about 660 nm to about 800 nm, of about 660 nm to about 710 nm, of about 660 nm to about 700 nm, of about 670 nm to about 700 nm, of about 670 nm to about 710 nm, of about 680 nm to 710 nm, of about 690 nm to 710 nm, of about 670 nm to about 690 nm, of about 700 nm, or of about 680 nm. The x-ray absorbing nanostructures can be selected from any nanostructure that is found to have these above properties.

The x-ray absorbing NSs can include a first component such as silicon carbide (SiC), silicon dioxide ($SiO_2$), hydroxyapatite, zinc-gallium-oxide, other suitable in-vivo biocompatible nanostructures, or a combination thereof. In some cases, the x-ray absorbing NSs can include a first component comprising silicon or germanium, magnesium, zinc, cadmium, mercury as group II elements, aluminum, gallium, indium as group III elements, nitrogen, phosphorus, arsenic, antimony as group V elements, oxygen as group VI elements, sulfur, selenium, or tellurium, or a combination thereof. In the NSs, the first component may be used alone or in combination of two or more. The first component can be present in an amount of 100% or less by weight, 99% or less by weight, 98% or less by weight, 97% or less by weight, 96% or less by weight, 95% or less by weight, 94% or less by weight, 93% or less by weight, 92% or less by weight, 91% or less by weight, 90% or less by weight, or 85% or less by weight. In some embodiments, the first component can be present in an amount from 50 to 100% by weight, from 80 to 100% by weight, from 90 to 100% by weight, from 80 to 98% by weight, from 90 to 98% by weight, from 95 to 98% by weight, from 85 to 97% by weight, or from 90 to 97% by weight, based on the total weight of the X-ray absorbing nanostructure.

The X-ray absorbing NS can further comprise a dopant, preferably a luminescent dopant. The dopant preferably has the ability to 'stop' x-rays, thus down converting the x-ray photon to a NIR photon. The dopant generally has a heavy atomic mass and encompasses heavy elements, including heavy metals. In some examples, the x-ray absorbing nanoparticle can comprise a dopant selected from europium III ($Eu^{3+}$), chromium III ($Cr^{3+}$), gold (Au), other x-ray absorbing heavy element (or heavy metal) dopants, or a combination thereof. The dopant can be present in an amount of 10% or less by weight, 9% or less by weight, 8% or less by weight, 7% or less by weight, 6% or less by weight, 5% or less by weight, 4% or less by weight, 3.5% or less by weight, 3% or less by weight, 2.5% or less by weight, 2% or less by weight, or 1.5% or less by weight. In some embodiments, the dopant can be present in an amount from 0.01 to 10% by weight, from 0.01 to 7.5% by weight, from 0.01 to 5% by weight, from 0.05 to 7.5% by weight, from 0.05 to 5% by weight, from 0.05 to 4% by weight, from 0.05 to 3.5% by weight, or from 0.05 to 3% by weight, based on the total weight of the X-ray absorbing nanostructure.

Preferred examples of x-ray absorbing NSs include nanowires and nanoparticles including for example, core/shell nanowires or core/shell nanoparticles. In some examples, the x-ray absorbing NSs can include a europium-doped $SiO_2$ nanoparticles (Eu—$SiO_2$), europium-doped hydroxyapatite nanoparticles (Eu—$HP_2$), $Cr^{3+}$ doped zinc-gallium-oxide nanoparticles (ZnGaO:Cr), $Cr^{3+}$ doped zinc-gallium-oxide with SiC core nanoparticles, SiC nanowires, or a combination thereof. The x-ray absorbing NSs can also be formed from any material that provides the above absorption and emission properties. Preferred materials for forming the nanostructures described herein include silicon carbide (SiC). SiC NSs have shown prior biocompatibility with little inflammatory or immunogenic responses.

The x-ray absorbing nanostructures as used in the methods described herein can be irradiated with x-ray radiation, i.e. electromagnetic radiation having a wavelength from about 0.01 to about 10 nm, using any available method that would be suitable for this purpose as would be selected by one of skill in the art. Numerous commercial x-ray sources are available and would be readily identified by one of skill in the art. In a typical embodiment, the x-ray source is a commercially available x-ray radiotherapy instrument. Upon irradiation with x-rays, the x-ray absorbing nanostructures described herein will release near-infrared light that can activate any antibody-photoabsorber conjugates present near the tumor of interest. In preferred embodiments, a low dose of x-ray radiation is used to reduce cytotoxic effects for healthy tissue, for example an x-ray radiation dose of about 0.1 Gy to about 2 Gy. In some embodiments, the x-ray radiation dose is no more than about 2 Gy, no more than about 1.5 Gy, no more than 1 Gy, no more than 0.5 Gy, or no more than 0.1 Gy.

X-Ray Absorbing Nanowires

In some embodiments, the x-ray absorbing nanostructure as used in the methods described herein is a nanowire. In some embodiments, the nanowires used in the methods described herein are silicon carbide (SiC) nanowires. Nanowires based on cubic silicon carbide (3C SiC) can be used and are readily synthesized via chemical vapor deposition, for example by the methods described in Negri, M. 2015; Fabbri, F. 2014; or Attolini, G. 2014. In some embodiments, the nanowires as used in the methods described herein can be composed of 3C SiC nanowires with silicon dioxide in a core/shell NW structure (3C—SiC/$SiO_2$ NWs). Nanowires with such a structure allow for optional surface functionalization if deemed necessary for the application, as described in Fabbri 2012a and Rossi 2013. In addition, the silicon dioxide shell enhances luminescence of the SiC core (see Fabbri 2010, Fabbri 2 2012, Fabbri 2014) when excited by highly energetic sources such as electron beams or x-rays (see Rossi 2015). This property enables 3C—SiC/$SiO_2$ NWs to act as radiation-induced scintillation nanostructures that generate NIR light capable of inducing NIR-PIT (Hanaoka 2015). In typical embodiments, the NWs are grown in tables having diameters ranging from about 40 to about 60 nm. After ball-milling, the NWs can be reduced to cylinders having lengths ranging from about 40-50 nm up to about 100 nm.

X-Ray Absorbing Nanoparticles

In other embodiments, the x-ray absorbing nanostructure as used in the methods described herein is a nanoparticle. In some embodiments, the nanoparticles used in the methods described herein comprise silicon carbide nanoparticles (SiC NPs) (Vöros 2010a, Vöros 2010b; Vöros 2011; Somogyi 2012). Representative examples of SiC NPs for use include those that act as fluorophores for in vivo bioimaging (Beke 2011; Beke 2013a; Beke 2013b). 1-3 nm SiC NPs are water soluble and exhibit stable luminescence in the blue region where the maximum of the intensity typically lies at 450 nm (~2.7 eV) and has a broad luminescence band till 700 nm (Beke 2015). Control over the entire process by synthesizing microcrystalline cubic silicon carbide powder and then production of colloid SiC NPs by wet chemical etching allows tuning of the optical and other properties of SiC NPs by altering their surface (Szekrényes 2015; Beke 2016). Beside the surface terminations, the characteristic size of SiC NPs strongly affects the type of luminescence (Beke 2015). x-ray induced optical luminescence has been previously demonstrated on relatively large (45-55 nm) SiC particles (Liu 2010). In some embodiments, the SiC NPs have a diameter from about 30 nm to about 50 nm. In other embodiments, the SiC NPs have a diameter of less than about 10 nm.

In some method embodiments, the nanoparticles may have a diameter of at least about 1 nm, at least about 10 nm, at least about 20 nm, at least about 30 nm, at least about 40 nm, at least about 50 nm, at least about 60 nm, at least about 70 nm, at least about 80 nm, at least about 90 nm, at least about 100 nm, at least about 110 nm, at least about 120 nm, at least about 130 nm, at least about 140 nm, at least about 150 nm, at least about 160 nm, at least about 170 nm, at least about 180 nm, at least about 190 nm, at least about 200 nm, at least about 210 nm, at least about 220 nm, at least about 240 nm, at least about 250 nm, at least about 270 nm, at least about 280 nm, at least about 300 nm, at least about 320 nm, at least about 350 nm, at least about 375 nm, or at least 400 nm. In some embodiments, the nanoparticles may have a diameter of less than 500 nm, less than 450 nm, less than 400 nm, less than 380 nm, less than 350 nm, less than 320 nm, less than 300 nm, less than 290 nm, less than 280 nm, less than 270 nm, less than 250 nm, less than 220 nm, less than 200 nm, less than 180 nm, less than 170 nm, less than 160 nm, less than 150 nm, less than 140 nm, less than 120 nm, less than 110 nm, less than 100 nm, less than 90 nm, less than 80 nm, less than 70 nm, less than 60 nm, less than 50 nm, less than 40 nm, less than 35 nm, or less than 30 nm. The diameter of the nanoparticles can range from any of the minimum values described above to any of the maximum values described above, for example from 1 nm to 500 nm, 10 nm to 500 nm, 50 nm to 500 nm, 100 nm to 500 nm, from 1 nm to 350 nm, 10 nm to 350 nm, 50 nm to 350 nm, 100 nm to 350 nm, from 10 nm to 300 nm, 100 nm to 300 nm, 150 nm to 300 nm, 100 nm to 250 nm, 150 nm to 250 nm, from 1 nm to 100 nm, 1 nm to 90 nm, 5 nm to 100 nm, 5 nm to 90 nm, from 5 nm to 75 nm, from 5 nm to 50 nm, 10 nm to 100 nm, 10 nm to 90 nm, 10 nm to 80 nm, from 10 nm to 75 nm, from 10 nm to 60 nm, 10 nm to 50 nm, 10 nm to 40 nm, 10 nm to 35 nm, or from 10 nm to 30 nm. This list is intended to be merely exemplary, and any of numerous combinations of minimum and maximum values described above may be used as a range of nanoparticle diameters.

In some embodiments, the methods comprise administering nanoparticles having a low polydispersity index, preferably a monodispersed size distribution. In some embodiments, the nanoparticles can have a polydispersity of less than 0.5, less than 0.4, less than 0.3, less than 0.2, or less than 0.15.

The x-ray absorbing NS can be functionalized with a surface-bound molecule. Such surface bound molecules can be selected from a surfactant, a dispersant, a targeting agent which facilitates delivery of the nanoparticle to the cancer cell, or a combination thereof. The surfactant or dispersant can facilitate dispersion of the nanoparticle in a solvent with minimal sedimentation. For example, the surface of the Eu-doped silica nanoparticles exhibits a large amount of —OH groups and therefore it can be easily functionalized to avoid sedimentation processes. Eu-doped hydroxyapatite nanoparticles primarily includes calcium phosphate exhibiting different surface chemical groups: —$Ca^{2+}$; —OH; and —$PO_4^{2-}$. In some examples, the hydroxyapatite can be functionalized using surface —OH as anchoring site for amino group —$NH_2$ or acid groups such as L-glutamic and succinic acid. $Ca^{2+}$ can bind $NH_2$ species as well. The surface of the zinc-gallium-oxide nanoparticles doped with $Cr^{3+}$ and SiC contains positively charged ions and oxygen groups. The surface can be easily modified with surfactants. In some examples, surface modifications can include functionalization with polyalkyleneimine such as PEI (polyethyleneimine), BSA (bovin serum albumin), PVA (polyvinyl alcohol), or PEG (polyethylene glycol).

In some embodiments, the nanoparticles may further be functionalized with one or more targeting agents. As used herein, a "targeting agent" is a molecule or composition comprising more than one molecule which facilitates delivery of the nanoparticles to one or more tissue types or cell types. As a nonlimiting example, a targeting agent can be an antibody which binds a receptor present in the tissue types or cell types. As another nonlimiting example, the targeting agent can be a molecule which is chemically altered in the environment of the tissue types or cell types, for example a molecule which degrades in hypoxic or acidic conditions of tumor microenvironments. In some embodiments, the targeting agent targets cancer cells or tumor cells. In some embodiments, the targeting agent promotes cellular attachment. In some embodiments, the targeting agent comprises an amino acid sequence.

The NSs may be formulated in a vehicle in a range of concentrations. Typically, the concentration of nanoparticles in a vehicle is a therapeutic amount when administered to a subject. In some embodiments, a vehicle may be formulated with NSs at a concentration of at least 1 ppm, 5 ppm, 10 ppm, 25 ppm, 50 ppm, 100 ppm, 200 ppm, 300 ppm, 400 ppm, 500 ppm, 600 ppm, 700 ppm, 800 ppm, 900 ppm, 1,000 ppm, 1,500 ppm, 2,000 ppm, 5,000 ppm, 10,000 ppm, 50,000 ppm, or at least 100,000 ppm. In some embodiments, a vehicle may be formulated with NSs at a concentration of less than 500,000 ppm, 100,000 ppm, 50,000 ppm, 10,000 ppm, 5,000 ppm, 2,000 ppm, 1,000 ppm, 900 ppm, 800 ppm, 700 ppm, 600 ppm, 500 ppm, 400 ppm, 300 ppm, 200 ppm, 100 ppm, 50 ppm, 25 ppm, or less than 10 ppm. Types of Cancer The methods described herein can be used in the treatment of a cancer. In some embodiments, treatment refers to partial or complete alleviation, amelioration, relief, inhibition, delaying onset, reducing severity and/or incidence of the cancer in the patient.

The terms, "improve," "increase," "reduce," "decrease," and the like, as used herein, indicate values that are relative to a control. In some embodiments, a suitable control is a baseline measurement, such as a measurement in the same individual prior to initiation of the treatment described herein, or a measurement in a control individual (or multiple control individuals) in the absence of the treatment described herein.

The individual (also referred to as "patient" or "subject") being treated is an individual (fetus, infant, child, adolescent, or adult human) having a disease, disorder, or condition, or having the potential to develop a disease, disorder, or condition.

In some embodiments, the individual is an individual who has been recently diagnosed with a cancer. Typically, early treatment (treatment commencing as soon as possible after diagnosis) is important, to minimize the effects of a cancer and to maximize the benefits of treatment.

In preferred embodiments, the cancer is a deep-tissue cancer that is not properly penetrated by near-infrared light delivered through the skin and that would typically require surgical or endoscopic methods for NIR light delivery. For example, the cancer can be a locally advanced, deep visceral cancer.

Representative examples of cancers that can be treated by the methods described herein include, but are not limited to: brain tumors such as for example acoustic neurinoma, astrocytomas such as fibrillary, protoplasmic, gemistocytary, anaplastic, pilocytic astrocytomas, glioblastoma, gliosarcoma, pleomorphic xanthoastrocytoma, subependymal large-cell giant ceil astrocytoma and desmoplastic infantile astrocytoma, brain lymphomas, brain metastases, hypophyseal tumor such as prolactinoma, hypophyseal incidentaloma, HGH (human growth hormone) producing adenoma and corticotrophic adenoma, craniopharyngiomas, medulloblastoma, meningeoma and oligodendroglioma; nerve tumors such as for example tumors of the vegetative nervous system such as neuroblastoma, ganglioneuroma, paraganglioma (pheochromocytoma, chromaffinoma) and giomuscaroticum tumor, tumors on the peripheral nervous system such as amputation neuroma, neurofibroma, neurinoma (neurilemmoma, Schwannoma) and malignant Schwannoma, as well as tumors of the central nervous system such as brain and bone marrow tumors; intestinal cancer such as for example carcinoma of the rectum, colon, anus and duodenum; carcinoma of the spleen; eyelid tumors (basalioma or adenocarcinoma of the eyelid apparatus); retinoblastoma; carcinoma of the pancreas; carcinoma of the bladder; lung tumors (bronchial carcinoma.—small-cell lung cancer (SCLC), non-small-cell lung cancer (NSCLC) such as for example spindle-cell plate epithelial carcinomas, adenocarcinomas (acinay, paillary, bronchiolo-alveolar) and large-ceil bronchial carcinoma (giant cell carcinoma, clear-cell carcinoma)); breast cancer such as ductal, lobular, mucinous or tubular carcinoma, Paget' s carcinoma; non-Hodgkin's lymphomas (B-lymphatic or T-lymphatic NHL) such as for example hair cell leukemia, Burkitt's lymphoma or mucosis fungoides; Hodgkin's disease; uterine cancer (corpus carcinoma or endometrial carcinoma); CUP syndrome (Cancer of Unknown Primary); ovarian cancer (ovarian carcinoma mucinous or serous cystoma, endometriodal tumors, clear cell tumor, Brenner's tumor); gall bladder cancer; bile duct cancer such as for example Klatskin tumor, testicular cancer (germinal or non-germinal germ cell tumors); laryngeal cancer such as for example supra-glottal, glottal and subglottal tumors of the vocal cords; bone cancer such as for example osteochondroma, chondroma, chondroblastoma, chondromyxoid fibroma, chondrosarcoma, osteoma, osteoid osteoma, osteoblastoma, osteosarcoma, non-ossifying bone fibroma, osteofibroma, desmoplastic bone fibroma, bone fibrosarcoma, malignant fibrous histiocyoma, osteoclastoma or giant cell tumor, E wing's sarcoma, and plasmocytoma, head and neck tumors (HNO tumors) such as for example tumors of the lips, and oral cavity (carcinoma of the lips, tongue, oral cavity), nasopharyngeal carcinoma (tumors of the nose, lymphoepithelioma), pharyngeal carcinoma, oropharyngeal carcinomas, carcinomas of the tonsils (tonsil malignoma) and (base of the) tongue, hypopharyngeal carcinoma, laryngeal carcinoma (cancer of the larynx), tumors of the paranasal sinuses and nasal cavity, tumors of the salivary glands and ears; liver cell carcinoma (hepatocellular carcinoma (HCC); leukemias, such as for example acute leukemias such as acute lymphatic/lymphoblastic leukemia (ALL), acute myeloid leukemia (AML); chronic lymphatic leukemia (CLL), chronic myeloid leukemia (CML); stomach cancer (papillary, tubular or mucinous adenocarcinoma, adenosquamous, squamous or undifferentiated carcinoma; malignant melanomas such as for example superficially spreading (SSM), nodular (NMM), lentigo-maligna (LMM), acral-lentiginous (ALM) or amelanotic melanoma (AMM); renal cancer such as for example kidney cell carcinoma (hypernephroma or Grawitz's tumor); oesophageal cancer; penile cancer, prostate cancer; vaginal cancer or vaginal carcinoma; thyroid carcinomas such as for example papillary, follicular, medullary or anaplastic thyroid carcinoma; thymus carcinoma (thymoma); cancer of the urethra (carcinoma of the urethra, urothelial carcinoma) and cancer of the vulva.

Methods of Treatment

The methods described herein rely on the use of nanostructures, such as $Eu^{3+}$-doped silica or hydroxyapatite nanoparticles, or chromium (III) doped zinc-gallium-oxide nanoparticles with or without a SiC cores, that can be excited by x-rays to emit NIR light, thus permitting deep-tissue treatment with NIR-PIT. As x-rays readily penetrate through tissues, the NSs can be sources of NIR light deep within the tumor. Prior studies have shown that while a single exposure of APC followed by a single dose of NIR light is effective in knocking down cancer cells, it is not adequate to completely kill the tumor, likely due to heterogeneous distribution of the APC within the tumor. However, multiple exposures of APC and light, separated by hours to days, are much more effective and have resulted in cures both in animals and humans. However, repeated light exposures are not practical for deep visceral tumors. The APC demonstrates a relatively long circulation time due to its large molecular size. Thus, after the first light exposure, additional circulating APCs enter the tumor and bind to remaining tumor cells. Additionally, since NIR-PIT kills tumor cells but not vascular endothelium, the vessels are left intact, leading to a 24 fold increase in the deposition of macromolecules as large as 200 nm in treated tumors, an effect that has been termed Super Enhanced Permeability and Retention (SUPR) (Kobayashi and Choyke 2015; Sano 2013). The methods described herein seek to take advantage of the SUPR effect after an initial NIR-PIT treatment as this is ideal for concentrating nanostructures at the tumor site. After an initial NIR-PIT session in a deep tumor using surgery or endoscopy to initially deliver NIR light, x-ray excitable nanostructures are administered which penetrate the tumor due to the SUPR effect. The initial NIR-PIT can kill up to approximately 70% of the tumor but the tumor will regrow if $2^{nd}$ and $3^{rd}$ light treatments are not added. SUPR should lead to high drug accumulations in tumors but not in normal organs due to the SUPR effect; a 10-20 fold increase in NS accumulation in the tumor treated with the initial NIR-PIT has been shown. As a specific example, an inoperable pancreatic tumor expressing mesothelin can be treated initially with an anti-mesothelin mAb-IR700 APC followed by endoscopically delivered NIR-PIT. X-ray excitable nanostructures can then be administered intravenously followed by repetitive doses of low dose external beam radiation to the pancreas separated by days. The inoperable tumor would receive multiple doses of light, only one of which is delivered in an invasive manner due to the NIR light emission of the administered x-ray absorbing NSs.

The nanostructures can induce light emission after x-ray excitation in a conventional radiotherapy clinical instrument. Thus, x-ray irradiation, with its desirable properties of deep tissue penetration, is converted to NIR light that activates an APC bound to the tumor. NIR-PIT only occurs where radiation is administered and only then, where the APC has bound to the tumor. After performing the first treatment of conventional NIR-PIT, tumors will develop a leaky vasculature known as the SUPR effect. Because of the SUPR effect (see Kobayashi 2013), these nanostructures will preferentially arrive within NIR-PIT treated tumors. Subsequent x-ray irradiation can result in complete treatment of the tumor. The methods described herein benefit from the close proximity of the nanostructures to the APC on the tumor cell which is estimated to be on the order of microns, preferably less than 50 microns such as10 microns. The APC preferentially accumulates only at sites where the tumor-specific antigen is overexpressed (at least 10,000 copies) and thus avoids normal tissue. The SUPR effect can be used to preferentially accumulate the x-ray absorbing NSs within the tumor bed. In addition, x-ray radiation can be limited to known sites of disease. Thus, even a low level of x-ray induced NIR could produce effective local treatments. The dose of radiation (0.1 to 2 Gy) needed has little direct cytotoxic effects on healthy tissue and must be viewed in comparison to other toxic therapies (including clinical radiation therapy) that are often used in treating cancers.

Thus, a method is provided for the treatment of a cancer in a subject in need thereof comprising:

(a) administering a therapeutically effective amount of an antibody-photoabsorber conjugate (APC) to the subject, wherein upon administration the APC is at least partially taken up into the cancer tissue and binds to a cell surface protein present within the cancer tissue;

(b) optionally exposing the cancer tissue to near-infrared (NIR) light;

(c) administering a therapeutically effective amount of an x-ray absorbing nanostructure (NS) to the subject, wherein the x-ray absorbing NS is at least partially taken up into the cancer tissue upon administration;

(d) exposing the cancer tissue to x-ray radiation, wherein upon exposure of the cancer tissue to x-ray radiation, the x-ray absorbing NS absorbs the x-ray radiation and emits NIR light; and (e) optionally repeating steps (c) and (d) one or more times. In one embodiment, the antibody-photoabsorber conjugate is an IR700 conjugate. In one embodiment, the antibody-photoabsorber conjugate is a cetuximab-IR700 conjugate. In one embodiment, the antibody-photoabsorber conjugate is a panitumumab-IR700 conjugate. In one embodiment, the x-ray absorbing nanostructure is nanowire. In one embodiment, the x-ray absorbing nanostructure is a nanoparticle. In one embodiment, the x-ray absorbing nanostructure is a silicon carbide (SiC) nanowire. In one embodiment, the x-ray absorbing nanostructure is a SiC-core/$SiO_2$ shell nanowire. In one embodiment, the x-ray absorbing nanostructure is a silicon carbide (SiC) nanoparticle. In one embodiment, the x-ray absorbing nanostructure is a Eu-doped silica nanoparticle. In one embodiment, the x-ray absorbing nanostructure is a Eu-doped hydroxyapatite nanoparticle. In one embodiment, the x-ray absorbing nanostructure is a chromium (III) doped zinc-gallium-oxide nanoparticle. In one embodiment, the x-ray absorbing nanostructure is a chromium (III) doped zinc-gallium-oxide shell with SiC core nanoparticle. In one embodiment, the cancer is a deep-tissue cancer.

In other embodiments, a method is provided for the treatment of a deep-tissue cancer in a subject in need thereof comprising:

(a) administering a therapeutically effective amount of an antibody-photoabsorber conjugate (APC) to the subject, wherein upon administration the APC is at least partially taken up into the cancer tissue and binds to a cell surface protein present within the cancer tissue;

(b) optionally exposing the cancer tissue to near-infrared (NIR) light;

(c) administering a therapeutically effective amount of an x-ray absorbing nanostructure (NS) to the subject, wherein the x-ray absorbing NS is at least partially taken up into the cancer tissue upon administration;

(d) exposing the cancer tissue to x-ray radiation, wherein upon exposure of the cancer tissue to x-ray radiation, the x-ray absorbing NS absorbs the x-ray radiation and emits NIR light; and (e) optionally repeating steps (c) and (d) one or more times. In one embodiment, the antibody-photoabsorber conjugate is an IR700 conjugate. In one embodiment, the antibody-photoabsorber conjugate is a cetuximab-IR700 conjugate. In one embodiment, the antibody-photoabsorber conjugate is a panitumumab-IR700 conjugate. In one embodiment, the x-ray absorbing nanostructure is nanowire. In one embodiment, the x-ray absorbing nanostructure is nanoparticle. In one embodiment, the x-ray absorbing nanostructure is a silicon carbide (SiC) nanowire. In one embodiment, the x-ray absorbing nanostructure is a SiC-core/$SiO_2$ shell nanowire. In one embodiment, the x-ray absorbing nanostructure is a silicon carbide (SiC) nanoparticle. In one embodiment, the x-ray absorbing nanostructure is a Eu-doped silica nanoparticle. In one embodiment, the x-ray absorbing nanostructure is a Eu-doped hydroxyapatite nanoparticle. In one embodiment, the x-ray absorbing nanostructure is a chromium (III) doped zinc-gallium-oxide nanoparticle. In one embodiment, the x-ray absorbing nanostructure is a chromium (III) doped zinc-gallium-oxide shell with SiC core nanoparticle. In one embodiment, the cancer is a deep-tissue cancer.

In other embodiments, a method is provided for the treatment of a cancer in a subject in need thereof comprising:

(a) administering a therapeutically effective amount of an antibody-photoabsorber conjugate (APC) to the subject, wherein upon administration the APC is at least partially taken up into the cancer tissue and binds to a cell surface protein present within the cancer tissue;

(b) optionally exposing the cancer tissue to near-infrared (NIR) light;

(c) administering a therapeutically effective amount of silicon carbide (SiC) nanowires, wherein the SiC nanowires are at least partially taken up into the cancer tissue upon administration;

(d) exposing the cancer tissue to x-ray radiation, wherein upon exposure of the cancer tissue to x-ray radiation, the SiC nanowires absorb the x-ray radiation and emit NIR light; and optionally repeating steps (c) and (d) one or more times. In one embodiment, the antibody-photoabsorber conjugate is an IR700 conjugate. In one embodiment, the antibody-photoabsorber conjugate is a cetuximab-IR700 conjugate. In one embodiment, the antibody-photoabsorber conjugate is a panitumumab-IR700 conjugate. In one embodiment, the cancer is a deep-tissue cancer.

In other embodiments, a method is provided for the treatment of a cancer in a subject in need thereof comprising:

(a) administering a therapeutically effective amount of an antibody-photoabsorber conjugate (APC) to the subject, wherein upon administration the APC is at least partially taken up into the cancer tissue and binds to a cell surface protein present within the cancer tissue;

(b) optionally exposing the cancer tissue to near-infrared (NIR) light;

(c) administering a therapeutically effective amount of silicon carbide (SiC) nanoparticles, wherein the SiC nanoparticles are at least partially taken up into the cancer tissue upon administration;

(d) exposing the cancer tissue to x-ray radiation, wherein upon exposure of the cancer tissue to x-ray radiation, the SiC nanoparticles absorb the x-ray radiation and emit NIR light; and optionally repeating steps (c) and (d) one or more times. In one embodiment, the antibody-photoabsorber conjugate is an IR700 conjugate. In one embodiment, the antibody-photoabsorber conjugate is a cetuximab-IR700 conjugate. In one embodiment, the antibody-photoabsorber conjugate is a panitumumab-IR700 conjugate. In one embodiment, the cancer is a deep-tissue cancer.

In some embodiments, a method is provided for the treatment of a cancer in a subject in need thereof comprising:

(a) administering a therapeutically effective amount of an antibody-IR700 conjugate to the subject, wherein upon administration the antibody-IR700 conjugate is at least partially taken up into the cancer tissue and binds to a cell surface protein present within the cancer tissue;

(b) optionally exposing the cancer tissue to near-infrared (NIR) light;

(c) administering a therapeutically effective amount of an x-ray absorbing nanostructure (NS) to the subject, wherein the x-ray absorbing NS is at least partially taken up into the cancer tissue upon administration;

(d) exposing the cancer tissue to x-ray radiation, wherein upon exposure of the cancer tissue to x-ray radiation, the x-ray absorbing NS absorbs the x-ray radiation and emits NIR light; and optionally repeating steps (c) and (d) one or more times. In one embodiment, the x-ray absorbing nanostructure is nanowire. In one embodiment, the x-ray absorbing nanostructure is nanoparticle. In one embodiment, the x-ray absorbing nanostructure is a silicon carbide (SiC) nanowire. In one embodiment, the x-ray absorbing nanostructure is a SiC-core/$SiO_2$ shell nanowire. In one embodiment, the x-ray absorbing nanostructure is a silicon carbide (SiC) nanoparticle. In one embodiment, the x-ray absorbing nanostructure is a Eu-doped silica nanoparticle. In one embodiment, the x-ray absorbing nanostructure is a Eu-doped hydroxyapatite nanoparticle. In one embodiment, the x-ray absorbing nanostructure is a chromium (III) doped zinc-gallium-oxide nanoparticle. In one embodiment, the x-ray absorbing nanostructure is a chromium (III) doped zinc-gallium-oxide shell with SiC core nanoparticle.

Combination Therapies

In some embodiments, the methods described herein can further comprise administering an additional therapeutic agent. The additional therapeutic agent can be administered simultaneously, sequentially, or at distinct points in time as any of the steps of the methods described herein.

In some embodiments, the additional therapeutic agent can be selected from one or more chemotherapeutic agents. Representative examples of chemotherapeutics agents that can be used herein include, but are not limited to, hormones, hormone analogues and antihormones (e.g. tamoxifen, toremifene, raloxifene, fuivestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosinekinase inhibitors, such as for example gefitinib, lapatinib and trastuzumab); signal transduction inhibitors (e.g. imatinib and sorafenib); antimetabolites (e.g. antifolates such as methotrexate, premetrexed and raltitrexed, pyrimidine analogues such as 5-fluorouracil, capecitabine and gemcitabine, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa), antimitotic agents (e.g. Vinca alkaloids such as for example vinblastine, vindesin, vinorelbin and vincristine; and taxanes such as paclitaxel and docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastim, interferon alpha, leucovorin, rituximab, procarbazine, levamisole, mesna, mitotane, pamidronate and porfimer.

Methods of Administration

The antibody-photoabsorber conjugates (APCs) or x-ray absorbing nanostructures (NSs) described herein, i.e. the active components disclosed herein, i.e. the APCs and x-ray absorbing NSs described herein, can be administered by any suitable method and technique presently or prospectively known to those skilled in the art. For example, the active components described herein can be formulated in a physiologically- or pharmaceutically-acceptable form and administered by any suitable route known in the art including, for example, oral and parenteral routes of administering. As used herein, the term "parenteral" includes subcutaneous, intradermal, intravenous, intramuscular, intraperitoneal, and intrasternal administration, such as by injection. Administration of the active components of their compositions can be a single administration, or at continuous and distinct intervals as can be readily determined by a person skilled in the art.

The active components disclosed herein, and compositions comprising them, can also be administered utilizing liposome technology, slow release capsules, implantable pumps, and biodegradable containers. These delivery methods can, advantageously, provide a uniform dosage over an extended period of time.

The active components disclosed herein can be formulated according to known methods for preparing pharmaceutically acceptable compositions. Formulations are described in detail in a number of sources which are well known and readily available to those skilled in the art. For example, Remington's Pharmaceutical Science by E. W. Martin (1995) describes formulations that can be used in connection with the disclosed methods. In general, the active components disclosed herein can be formulated such that an effective amount of the active component is combined with a suitable carrier in order to facilitate effective administration of the active component. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 100% by weight of the total of one or more of the active component based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

The active components disclosed herein, and compositions comprising them, can be delivered to a cell either through direct contact with the ceil or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 2003/0032594 and 2002/0120100 disclose amino acid sequences that can be coupled to another composition and that allows the composition to be translocated across biological membranes. U.S. Application Publication No. 2002/0035243 also describes compositions for transporting biological moieties across cell membranes for intracellular delivery. Compounds can also be incorporated into polymers, examples of which include poly (D-L lactide-co-glycolide) polymer for intracranial tumors; poly [bis(p-carboxyphenoxy)propane:sebacic acid] in a 20:80 molar ratio (as used in GLIADEL); chondroitin; chitin, and chitosan.

The active components and their compositions disclosed herein can be administered intravenously, intramuscularly, or intraperitoneally by infusion or injection. Solutions of the active component can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active component, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating an active component disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions.

Useful dosages of the active agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

Also disclosed are pharmaceutical compositions that comprise an active component disclosed herein in combination with a pharmaceutically acceptable earner. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment if any, frequency of treatment, therapeutic ratio, as well as the severity and stage of the pathological condition.

Also disclosed are kits that comprise an active component disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer an active component or composition of the kit. Containers of the kit can be of any suitable material, e.g., glass, plastic, metal, etc., and of any suitable size, shape, or configuration. In one embodiment an active component disclosed herein is provided in the kit as a solid, such as a tablet, pill, or powder form. In another embodiment, an active component disclosed herein is provided in the kit as a liquid or solution. In one embodiment, the kit comprises an ampoule or syringe containing an active component disclosed herein in liquid or solution form.

EXAMPLES

Figure 3A:
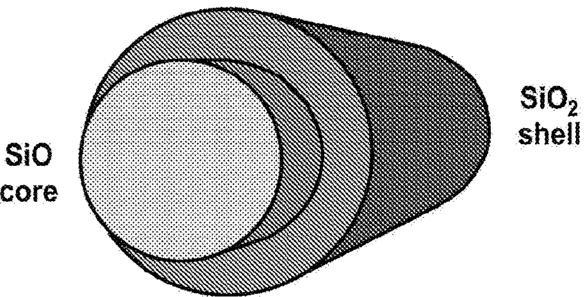
FIG. 3A is a scheme showing the general structure of a 3C—SiC/$SiO_2$ core/shell nanowire.
Figure 3B:
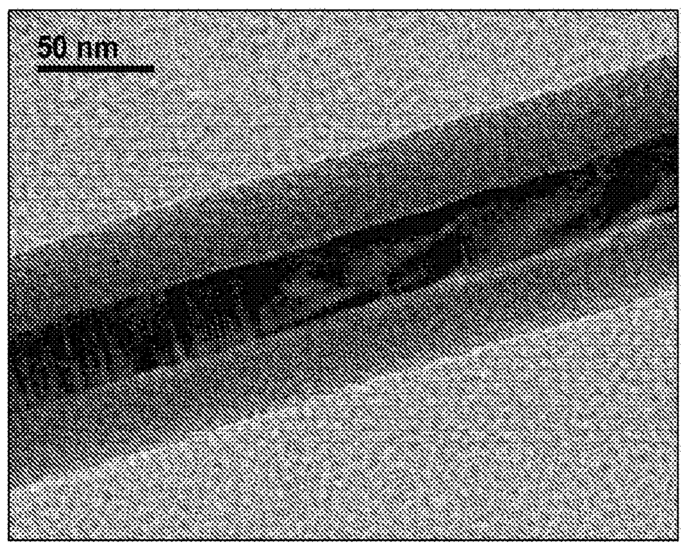
FIG. 3B is a transmission electron microscopy image of a 3C—SiC/$SiO_2$ core/shell nanowire. The orange box delineates the nanowire shape after milling.

Example 1. Optical Emission from Silicon Carbide Nanowires Via Cathodoluminescence Core shell 3C—SiC/$SiO_2$ nanowires are synthesized on silicon substrates in a chemical vapor deposition (CVD) reactor using carbon monoxide (CO) as a single precursor as described in Rossi 2016. The NWs are grown in tangles with diameters ranging between 40 and 60 nm. After proper ball milling procedures, the NWs are reduced to cylinders with the same diameters as above and lengths from 40-50 nm (FIG. 3 bottom left panel) up to 100 nm. The $SiO_2$ shell allows for easy NW surface functionalization and improves biocompatibility (Bigi 2007).

The core-to-shell ratio influences the luminescence of the nanosystem as proved by cathodoluminescence (CL) spectroscopy. CL uses highly energetic electrons in an SEM and is quite effective for stimulating optical emissions induced by energetic x-rays. The standard luminescence of the NWs is a broad visible emission (see FIG. 4). Gaussian deconvolution reveals that the emission is composed of three main features: the most intense at 2.69 eV, a shoulder at 2.38 eV, and a narrow emission at 2.00 eV. The emission at 2.38 eV is due to the 3C—SiC near-band edge emission (Ikeda and Matsunami 1980). At a core-to-shell ratio of 1:1, the silicon oxide shell is beneficial to enhance the light emission yield of the 3C—SiC core (Steuer 2014).

Figure 4:
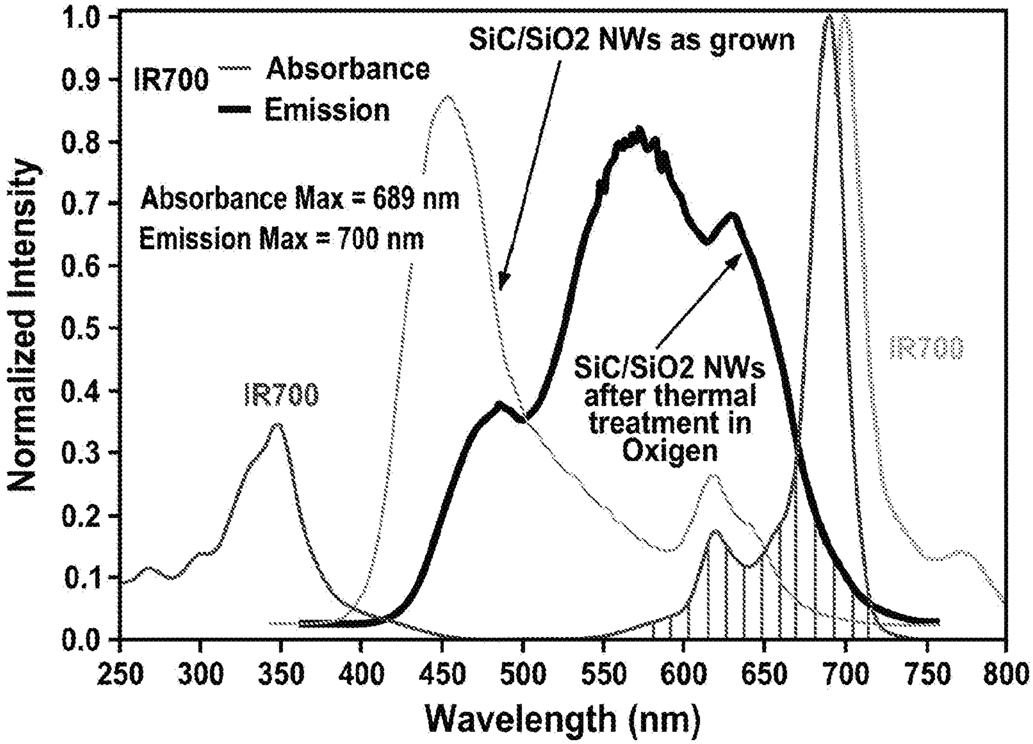
FIG. 4 is an optical emission spectrum for SiC nanowires via cathodoluminescence (CL). The black curve shows CL of SiC nanowires as grown. The red curve shows the CL emission of SiC nanowires after 2 hour thermal treatment in $O_2$. The relative weight of emission change and the spectrum red shifts with better overlap of the IR700 absorption band between 650-700 nm. The nanowire emission is not normalized to IR700. The x-axis measures wavelength in nanometers, and the y-axis shows normalized intensity.

Appropriate thermal treatments in an oxygen atmosphere result in excellent overlapping between the emission of the NWs and the absorption spectra of IR700 (red curve in FIG. 4 and vertical blue lines). Engineering the shell/core thickness ratio provides an additional red shift of the NW emission (see sub-aim 1.2) to match the IR-700 absorption edge.

Example 2. Synthesis and Optical Emission Silicon Carbide Nanoparticles

SiC NPs are synthesized as previously described (see Beke 2011; Beke 2013a; Beke 2013b). The ultra-small 1-3 nm SiC NPs shows strong surface related luminescence whereas >6 nm SiC NPs exhibit much weaker luminescence that either originates from the band edges or stacking fault defects inside SiC NPs. SiC NPs with a size of about 3-6 nm yield strong luminescence shifted toward the red region compared to that of 1-3 nm SiC NPs. These SiC NPs have an emission maximum at around 530 nm and shows significant emission even at 700 nm. SiC NPs exposed to high pH solvents show a new photoluminescence center appears that has a maximum emission at 620 nm with a broadband up to 770 nm. This new emission is due to the change in the surface potential. This confirms that the same type of emission can be achieved by changing the surface potential with surfactants to activate the 620 nm emission at neutral pH. 1-3 nm SiC NPs are water soluble and exhibit stable luminescence in the blue region (FIG. 5) where the maximum of the intensity typically lies at 450 nm (~2.7 eV) and has a broad luminescence band till 700 nm (Beke 2015). Full material control can occur over the entire process by synthesizing microcrystalline cubic silicon carbide powder and then production of colloid SiC NPs by wet chemical etching, making it possible to tune the optical and other properties of SiC NPs by altering their surface (Szekrényes 2015; Beke 2016). Beside the surface terminations, the characteristic size of SiC NPs strongly affects the type of luminescence (Beke 2015). The ultra-small 1-3 nm SiC NPs shows strong surface related luminescence whereas >6 nm SiC NPs exhibit much weaker luminescence that either originate from the band edges or stacking fault defects inside SiC NPs. SiC NPs with a size of about 3-6 nm yield strong luminescence shifted toward the red region compared to that of 1-3 nm SiC NPs. These SiC NPs have an emission maximum at around 530 nm and shows significant emission even at 700 nm. In addition, when these SiC NPs are exposed to high pH solvents then a new photoluminescence center appears that has a maximum emission at 620 nm with a broadband up to 770 nm. This new emission is due to the change in the surface potential. This confirms that the same type of emission can be achieved by changing the surface potential with surfactants to activate the 620 nm emission at neutral pH. The x-ray induced optical luminescence has been already demonstrated on relatively large (45-55 nm) SiC particles (Liu 2010), while x-ray absorption measurements were investigated on SiC NSs too (Wu 2009), SiC NPs exhibit luminescence with good overlap with IR700 excitation peak (dashed blue curve in FIG. 5). Thus, it is expected that efficient energy transfer will occur between SiC NPs and IR700 molecules in close proximity The wavelength of the luminescence can be tuned both by the size and the surface termination of the SiC NPs. Modification in SiC synthesis (changing the concentration of PTFE promoter, for example) can tune the yield of 3-6 nm particles. Post process separation techniques such as centrifugation and filtration are capable for further cleaning. The surface chemistry can be optimized to tune the wavelength of the luminescence in order to obtain the largest overlap with the absorption of IR700 in the wavelength region of 600-700 nm.

Example 3. Evaluation of Use of Low Energy X-Rays for X-ray Induced NIR-PIT

Figure 5:
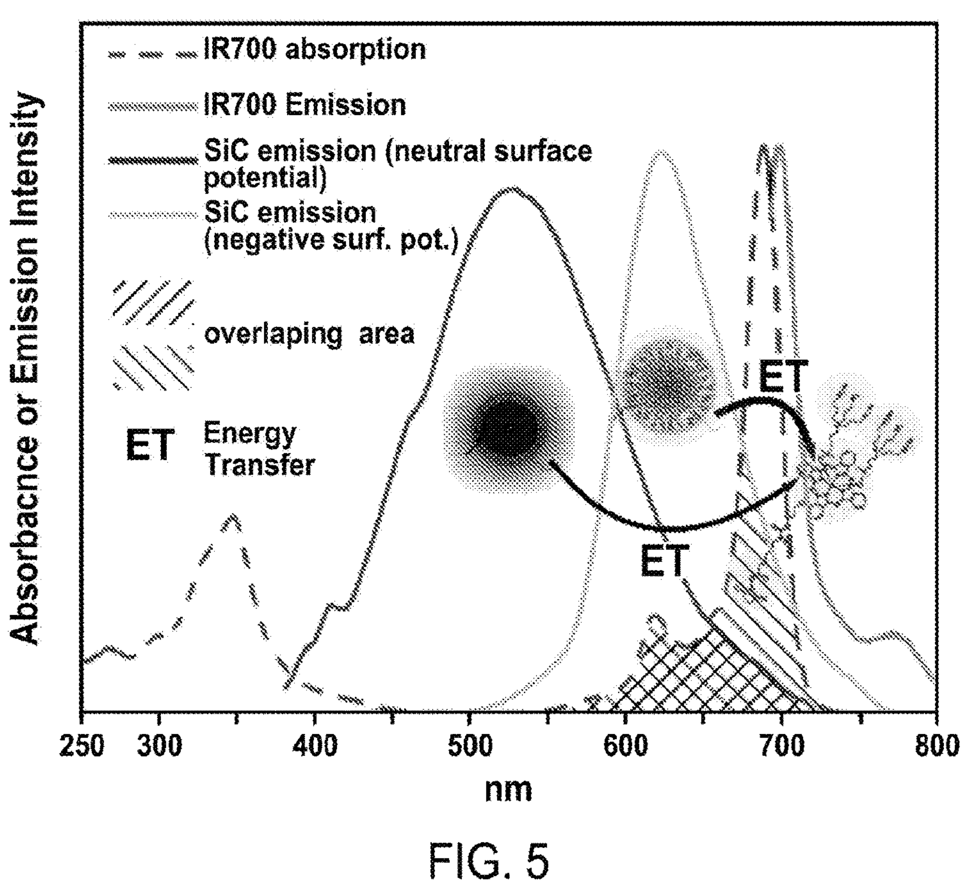
FIG. 5 is an absorbance/emission spectrum that shows the emission peaks of SiC nanoparticles overlapping with the IR700 absorption peak. The green curve is the neutral surface termination. The orange curve is the negative surface potential. The IR700 absorption (red curve) overlaps with the NIR emission from SiC nanostructures as shown. The x-axis measures wavelength in nanometers, and the y-axis measures either absorbance or emission intensity.
Figure 6:
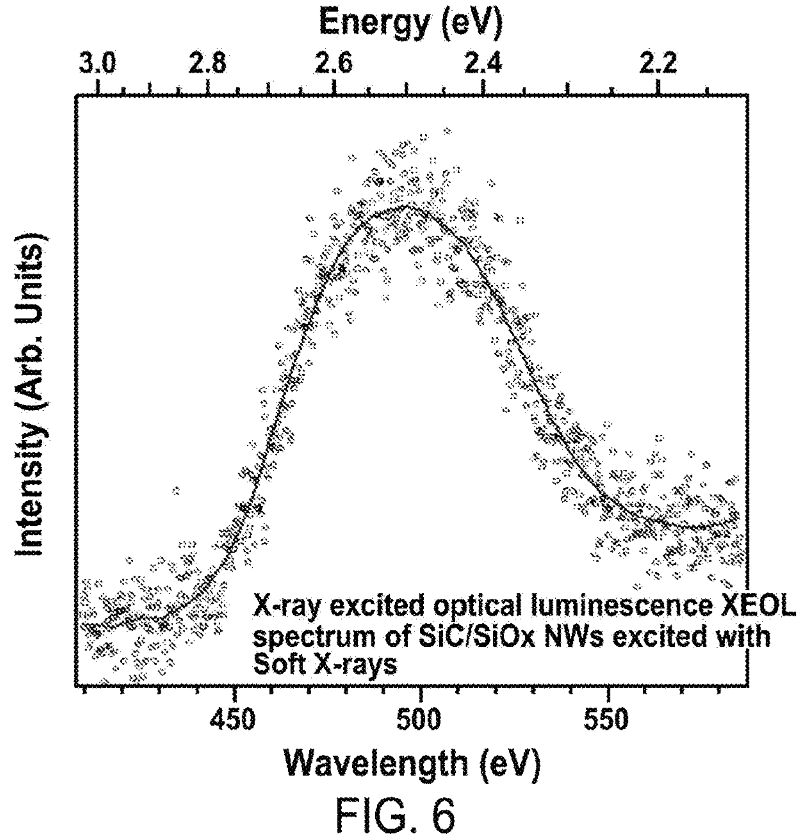
FIG. 6 is an x-ray excited optical luminescence spectrum for SiC/$SiO_2$ core/shell nanowires excited with soft x-rays. A 50% quantum efficiency is observed for converting x-rays to NIR light. The top x-axis is energy in electron volts and the bottom axis is wavelength in electron volts. The y-axis measures intensity.

To explore the possibility to use low energy x-rays (e.g. Computed Tomography-CT) and concurrently to maximize the overlap of NIR emission and IR700 absorption, x-ray induced optical luminescence studies in a Synchrotron Radiation facility on SiC, using low energies (<100 KeV). The proof of optical emission from SiC NWs under soft x-ray irradiation is reported in FIG. 6 where 50% quantum efficiency in the conversion of x-ray photons to optical photons was observed. While the luminescence peak is 200 nm from the optimum IR700 absorption peak, as stated earlier a red-shift is readily achieved via surface and/or thermal treatment of the SiC NWs. In addition, luminescence from SiC NWs under 6 MeV x-ray irradiation has also been obtained (Rossi 2015). The key idea is shown in FIG. 5 to harness SiC NPs for energy transfer into the IR700 complex (same applies to SiC NWs). The bioinert 3-6 nm SiC NPs exhibit such luminescence (orange and green curves) with good overlap with the absorption of the IR700 (dashed blue curve). Thus, it is expected that efficient energy transfer will occur between SiC NSs (NWs) and IR700 in close proximity Example 4. Evaluation of X-Ray Induced NIR-PIT In Vitro For these experiments, PanIR700 is synthesized so that an average of three IR700 molecules are bound to a single antibody. SDS-PAGE (sodium dodecyl sulfate polyacrylamide gel electrophoresis) is performed as a quality control for each conjugate.

Specific binding of pan-IR700 is confirmed with a blocking study using EGFR (epidermal growth factor receptor) -expressing A431 cells and MDA-MB-468-luc cells (stably luciferase-transfected). These cell lines are selected not only because they are well characterized but because they serve as a model for other cell types expressing different antigens for which monoclonal antibodies exist. To evaluate specific cell killing by NIR-PIT, 3T3 cells stably expressing DsRed (3T3/DsRed) are used as a negative control. A431 and MDA-MB-468-luc cells ($1\times10^5$) are incubated with pan-IR700 for 6 hr at 37° C. To detect the antigen specific localization of pan-IR700, fluorescence microscopy is performed. To validate the specific binding of pan-IR700, excess panitumumab (50 μg) is used to block 0.5 μg of pan-IR700. Ten thousand cells will be seeded on cover-glass-bottomed dishes and incubated for 24 hr. Pan-IR700 will then be added to the culture medium at 10 μg/mL and incubated at 37° C. The cells will then be washed with PBS; Cytox Blue is added into the media 30 min before therapy and is used to detect dead cells. SiC NSs are added at 5 different concentrations based on their x-ray dose-light emission efficiency determined in SA2. The cells are then exposed to increasing x-ray doses using an x-ray radiator (Faxitron) and serial fluorescence images are obtained. Cell viability is then measured. The filter is set to detect IR700 fluorescence with a 590-650 nm excitation filter, and a 665-740 nm bandpass emission filter.

In Vitro X-Ray Activated NIR-PIT

One hundred thousand cells are seeded into 24 well plates and incubated for 24 hr. The medium is then replaced with fresh culture medium containing 10 μg/mL of pan-IR700 and incubated for 6 hr at 37° C. After washing with PBS, phenol red free culture medium is added. Each SiC NS is added to each well plate in 5 concentrations (e.g. 0.01 mM, 0.1 mM, 1 mM, 10 mM, 100 mM, etc. to be determined by laboratory results). Then, cells are irradiated with an x-ray source (Faxitron) at 5 x-ray doses (1 mR, 10 mR, 100 mR, 1 R). The cytotoxic effects of NIR-PIT with pan-IR700 is determined by the luciferase activity analyzed on a bioluminescence imaging (BLI) system (Photon Imager; Biospace Lab, Paris, France). The optimized combination of SiC NS concentration and x-ray dose is established. The cytotoxic effects of NIR-PIT on A431 spheroids is determined with the Cytotoxicity Detection Kit Plus (Roche Applied Science, Basel, Switzerland), which can detect cell membrane damage. Day 7 spheroids, pre-incubated with pan-IR700 for 6 hr, will be washed with PBS, and transferred to 96 well plates (containing PBS), then irradiated with NIR-light. One hour later the results will be read out with a plate reader.

Example 5. Evaluation of X-Ray Induced NIR-PIT In Vivo

A431 and MDA-MB-468-luc cells is injected into the deep musculature of nude female mice with the tumor located below the skin surface to simulate a deep tumor and allowed to grow up to 0.5 cm diameter before treatment. Although the tumor is not located on the surface, a sufficient amount of NIR light penetrates to induce a partial response (~50-70%) with a single administration of NIR but does not completely kill the tumor. These tumor models are well known and do not metastasize under the growth conditions given. A vigorous SUPR response is seen after NIR-PIT. The test group contains animals with implanted tumors who receive panIR700, undergo initial NIR light treatment, followed by SiC NS injection and exposure to 5 serial daily doses of radiation. Tumor-bearing mice are randomized into groups of at least 10 animals per group for the following treatments: (1) No treatment (control), (2) APC only, (3) NIR only, (4) Radiation for 5 consecutive days only, (5) SiC nanoparticle only, (6) APC and NIR followed by SiC NP (no radiation), (7) APC (no NIR) followed by SiC NP and radiation for 5 days, and (8) APC and NIR followed by SiC NP and radiation for 5 days. Mice are monitored daily for toxicity, and tumor diameters are determined by ultrasound (as they will be deep to the surface) until the tumor diameter reaches 2 cm, whereupon the mice are euthanized with carbon dioxide. Bioluminescence imaging is performed daily in all groups. If the test group shows a superior response additional cycles are added in a separate group of animals. Mice are monitored closely for toxicity. At autopsy, organs are harvested to determine biodistribution of the SiC NSs using XEOL measurements ex vivo. Given the anticipated effect size, 10 animals per group are estimated to be sufficient to observe a difference in growth characteristics with sufficient power assuming expected experimental losses of 10-20%.

Example 6. Evaluation of SUPR Effect Using IR800-Labeled Silicon Carbide Nanoparticles In a separate experiment which seeks to investigate the vessel permeability and retention of SiC NSs within the tumor after NIR-PIT, each SiC NS is labeled with IR800, a fluorescent molecule. One hour after NIR-PIT (10 $J/cm^2$) 100 μg of SiC NS-IR800 are intravenously injected, and imaging studies are performed at the indicated time points with a Pearl Imager using 700 nm and 800 nm channels. For analyzing fluorescence intensities, mean intensities of IR800 of each ROI are calculated to estimate the increased leakage of SiC NSs following NIR-PIT and to semi-quantitate the amount of SiC NSs in the tumor. Additionally, in another set of 10 animals, the SiC NSs are injected immediately after NIR-PIT as described above in tumor-bearing mice. The mice are euthanized and organs dissected. The organs are irradiated at previously established x-ray doses with measurement of fluorescence specific for that SiC NS.

Example 7

While several treatments that aim to kill cancer cells while sparing normal cells are in development, no therapies have been developed for locally advanced, deep visceral cancers. Photoimmunotherapy is a targeted therapy for surface cancers with highly selective cell killing based on the use of an antibody-photoabsorber (such as IR700DX) conjugate and targeted low energy light therapy. In this example, luminescent nanostructures were used to convert medical x-rays to near IR (NIR) light to activate the IR700DX thus enabling deep-tissue cancer treatment.

Figure 7A:
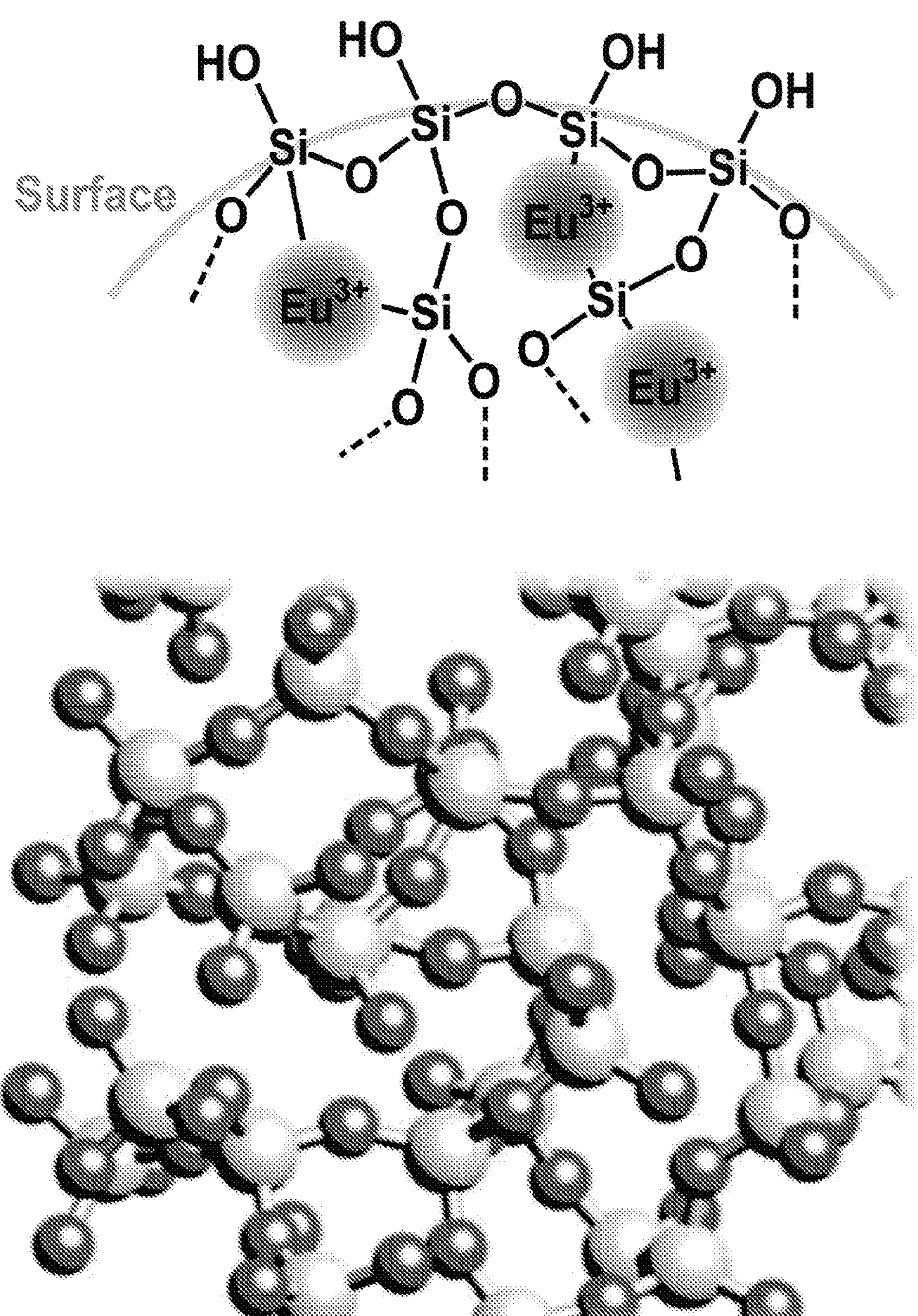
FIG. 7A is an diagram of a Eu-doped $SiO_2$ nanoparticle structure comprising amorphous silica.
Figure 7B:
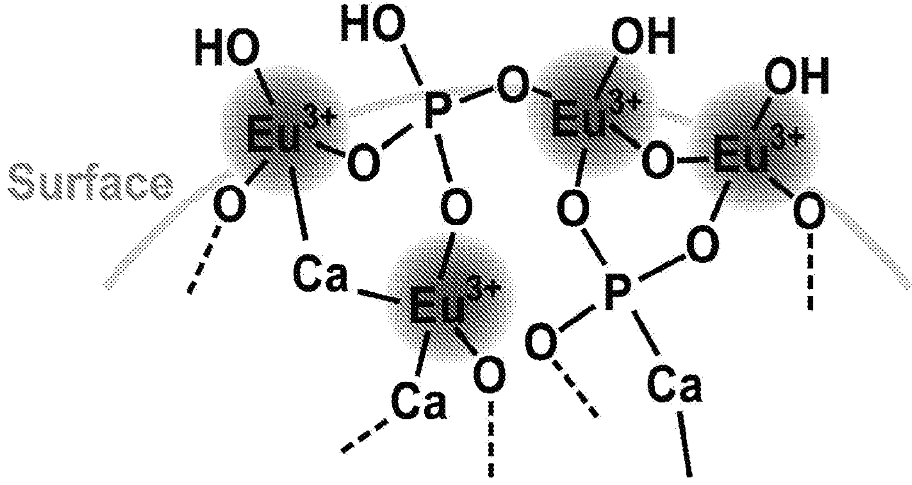
FIG. 7B is an diagram of a Eu-doped hydroxyapatite nanoparticle structure.
Figure 7B:
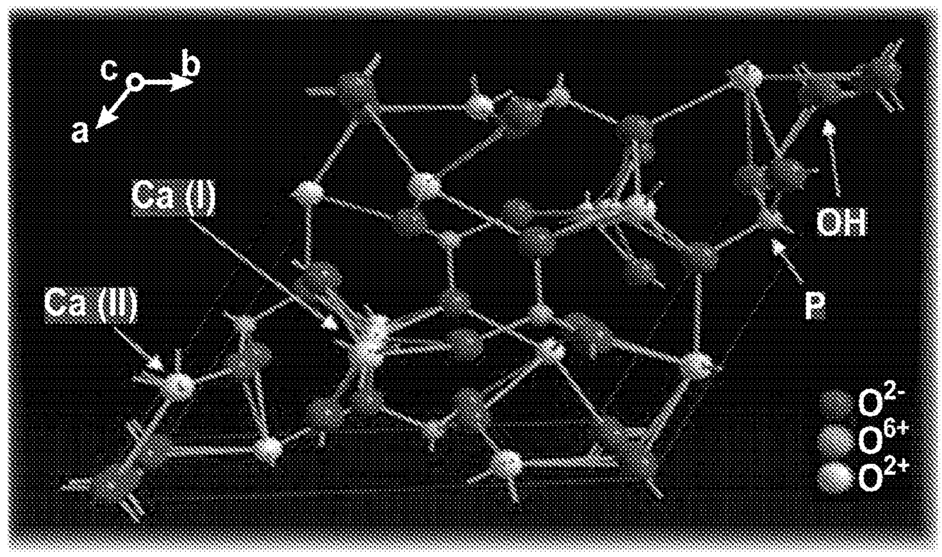
Figure 7C:
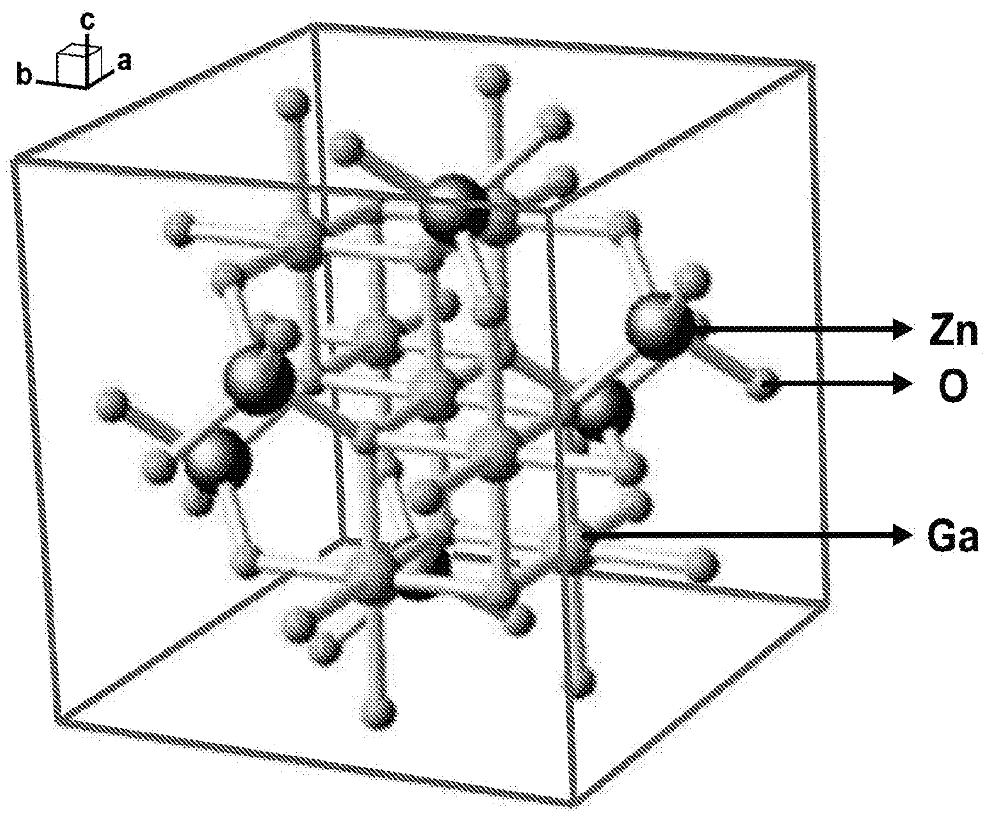
FIG. 7C is an diagram of a zinc-gallium-oxide nanoparticle (ZGO) shell doped with $Cr^{3+}$ with a SiC core nanoparticle.
Figure 7C:
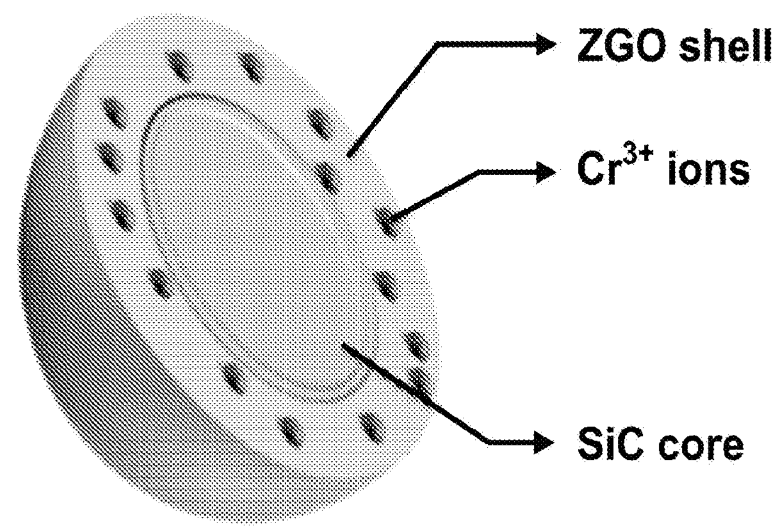
Figure 7D:
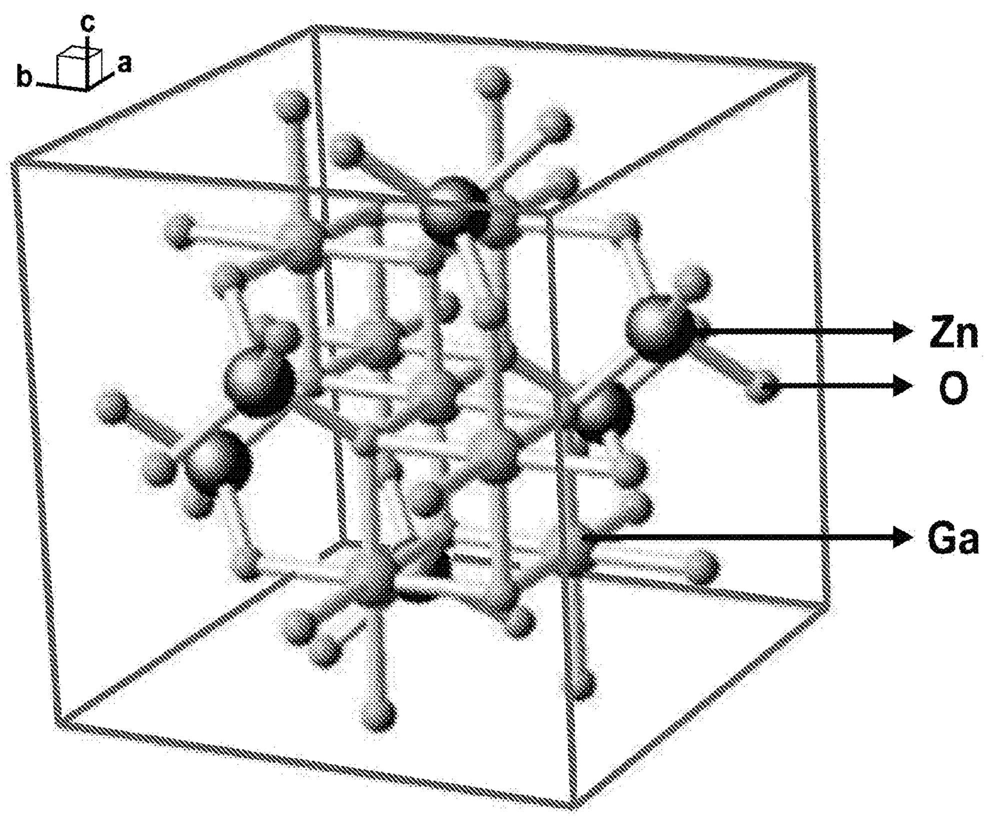
FIG. 7D is a diagram of a zinc-gallium-oxide nanoparticle (ZGO) doped with $Cr^{3+}$.
Figure 7D:
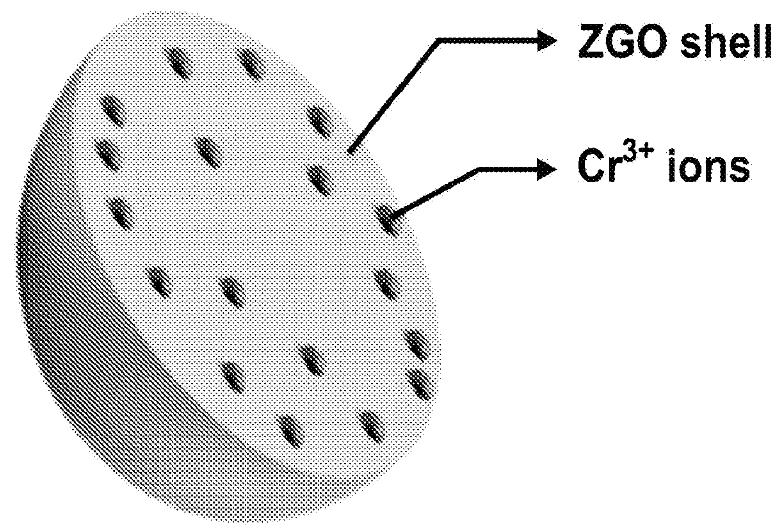

Nanoparticle Systems: Four types of nanoparticles (NPs) emitting at 700 nm under excitation with x-rays were prepared. Eu-Silica NPs (shown in FIG. 7A) comprises amorphous silica obtained by hydrolysis and condensation of TEOS. The $Eu^{3+}$ content is about 2-3%. The surface exhibits a large amount of —OH groups and therefore it can be easily functionalized to avoid sedimentation processes. FIG. 7B shows an image of a Eu-doped hydroxyapatite nanoparticles primarily consisting of calcium phosphate exhibiting different surface chemical groups: —$Ca^{2+}$; —OH (most relevant and abundant); —$PO_4^{2-}$. The $Eu^{3+}$ content is about 4%. HA can be functionalized mainly using surface —OH as anchoring site for amino group —$NH_2$ or acid such as L-glutamic and Succinic acid $Ca^+$ can bind $NH_2$ species as well. FIG. 7C is an image of a $Cr^{3+}$ doped zinc-gallium-oxide (ZGO) doped nanoparticle with a SiC core. The surface of the NPs contains positively charged ions and oxygen groups. The $Cr^{3+}$ content is estimated to be 0.05%. The surface can be easily modified with surfactants. Known surface modifications: PEI (polyethylenimine), BSA (bovin serum albumin), PVA (polyvinyl alcohol), and PEG (polyethylene glycol). FIG. 7D is an image of a $Cr^{3+}$ doped zinc-gallium-oxide (ZGO) nanoparticle. The surface of the NPs contains positively charged ions and oxygen groups. The $Cr^{3+}$ content is estimated to be 0.05%. The surface can be easily modified with surfactants. Known surface modifications: PEI (polyethylenimine), BSA (bovin serum albumin), PVA (polyvinyl alcohol), and PEG (polyethylene glycol).

Figure 8A:
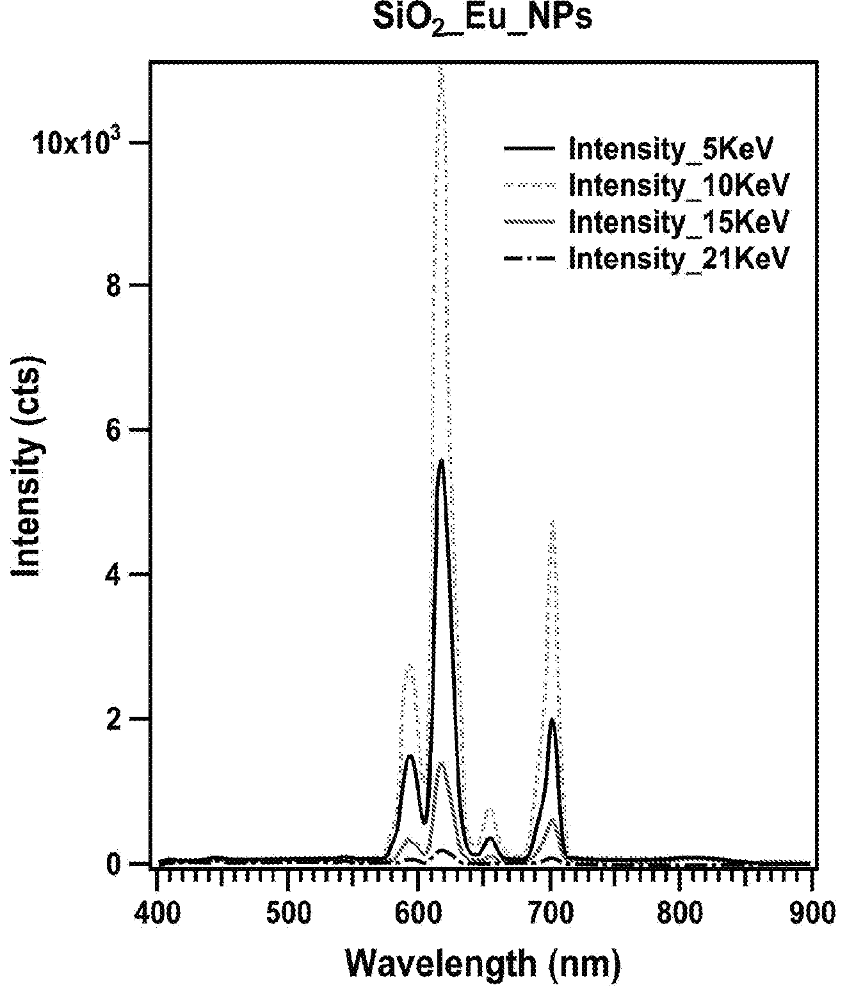
FIGS. 8A-8C are graphs showing x-ray-excited Optical Luminescence (XEOL) of a Eu-doped $SiO_2$ nanoparticle (FIG. 8A), Eu-doped (4%) hydroxyapatite nanoparticle (FIG. 8B), and zinc-gallium-oxide nanoparticle shell doped with $Cr^{3+}$ and a SiC core (FIG. 8C) @ 21 kVp on the Elettra Synchrotron. All nanoparticles display 700 nm emission.
Figure 8B:
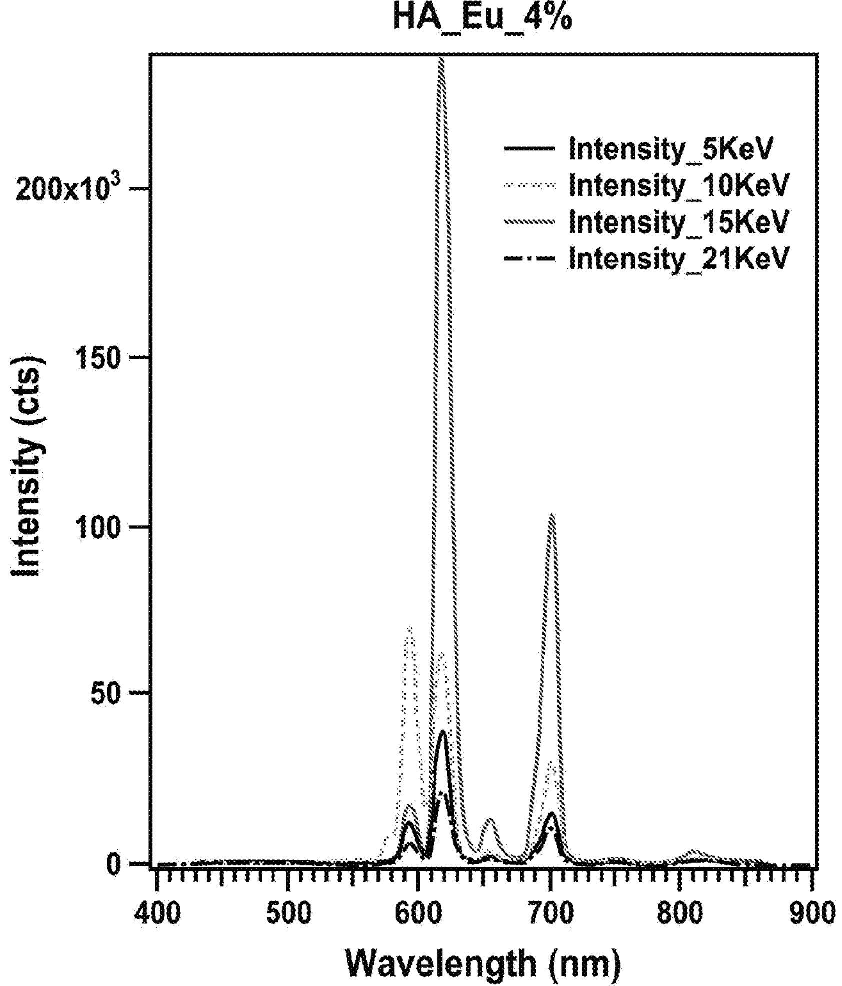
Figure 8C:
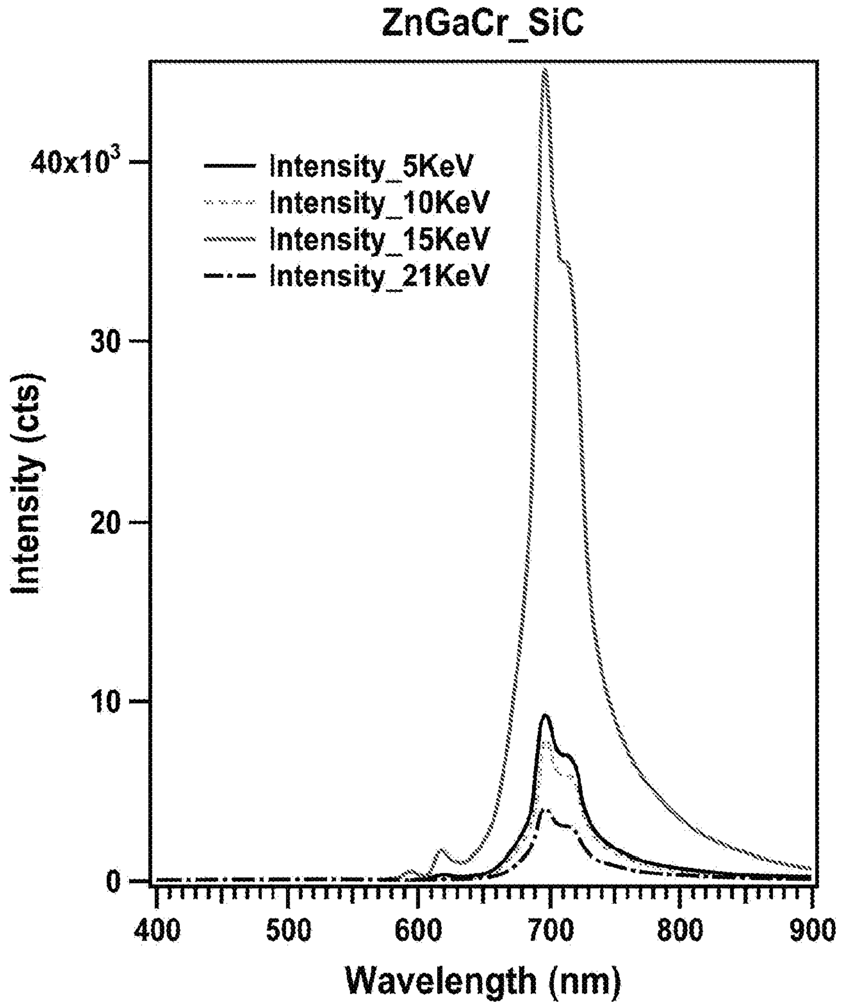

XEOL@21 kVp: x-rays of the NP System XEOL @ 21 kVp (on Elettra Synchrotron) were taken. FIGS. 8A-8C are graphs showing an x-ray-excited Optical Luminescence (XEOL) of a $SiO_2$_Eu_(FIG. 8A), HA_Eu_4%_(FIG. 8A), and ZiGaO:Cr_SiC (coreshell)_(FIG. 8A), nanoparticle system @ 21 kVp (Elettra Synchrotron). All NPs display 700 nm emission: ZGO:Cr_SiC was the brightest. ZGO:Cr was also studied with an XEOL intensity lower than ZGO:Cr (not shown).

Figure 9:
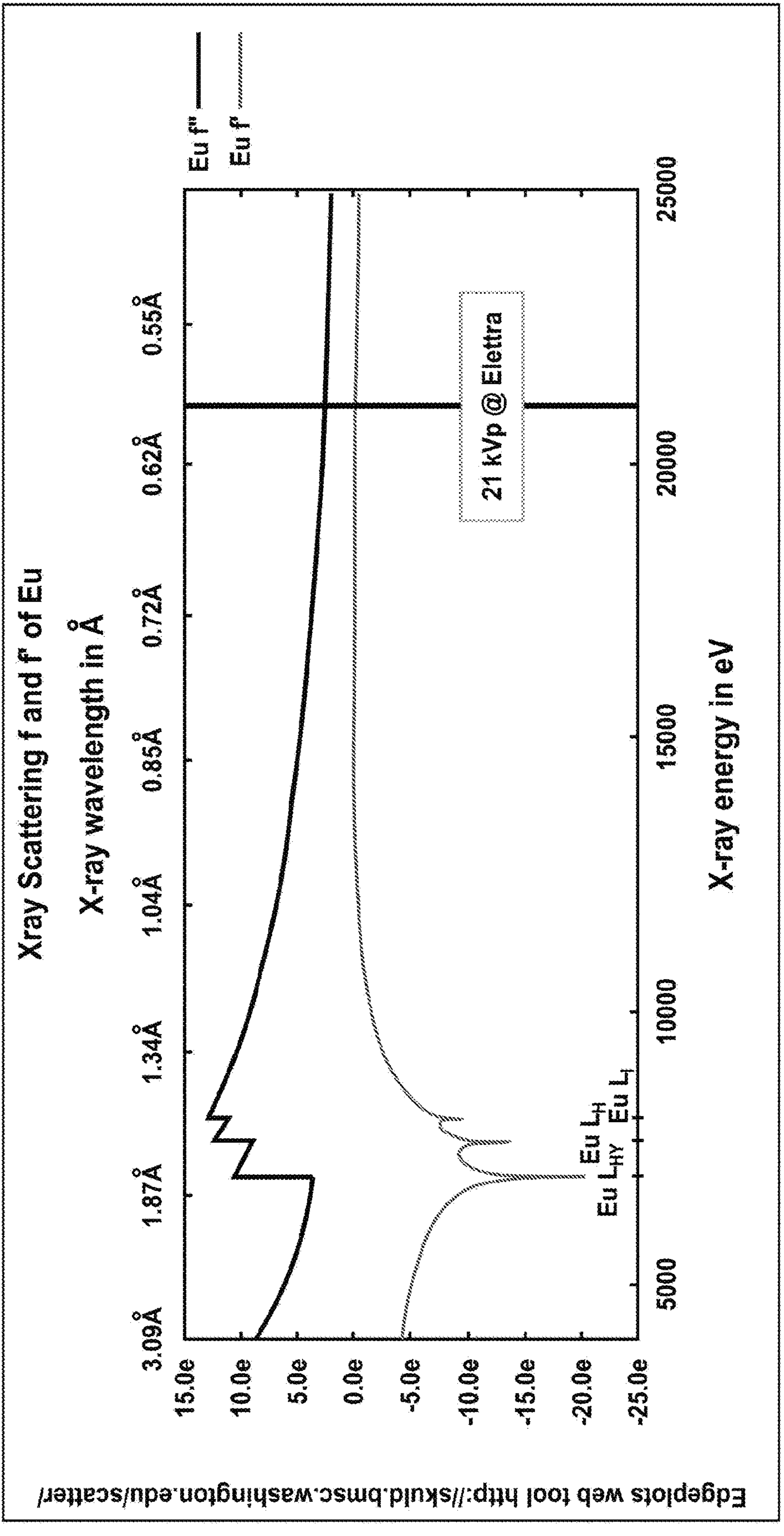
FIG. 9 is a graph showing the calculated x-ray scattering of $Eu^{3+}$ as a function of x-ray energy. XEOL observed @21 kVp is indicated and curve is asymptotically flat through the radiology x-ray source spectrum (~45 kVp to 120 kVp).

XEOL as a function of x-ray energy: FIG. 9 is a graph showing the x-ray cross-section of Eu as a function of x-ray energy in eV. Maximum photon energy (hv) @Elettra (XRD1) was 21 keV. Calculation of $Eu^{3+}$ interaction indicates nearly constant process for energies >20 keV: Thus XEOL is dependent only on x-ray photon flux for penetrating x-ray energies (i.e., hv>30 keV) such as those needed to penetrate the body such as a radiology x-ray machine. The x-ray response at 21 kVp (Elettra) should be similar at higher x-ray energies such as those found when using a radiology x-ray source. The synchrotron is a much more powerful x-ray beam (about 2× more than the radiology source). Therefore, if XEOL @21 kVp on Elettra can be observed, then it should be possible to stimulate XEOL on the radiology source. In the present examples, XEOL on the radiology tool have been observed (FIG. 12).

Figure 10A:
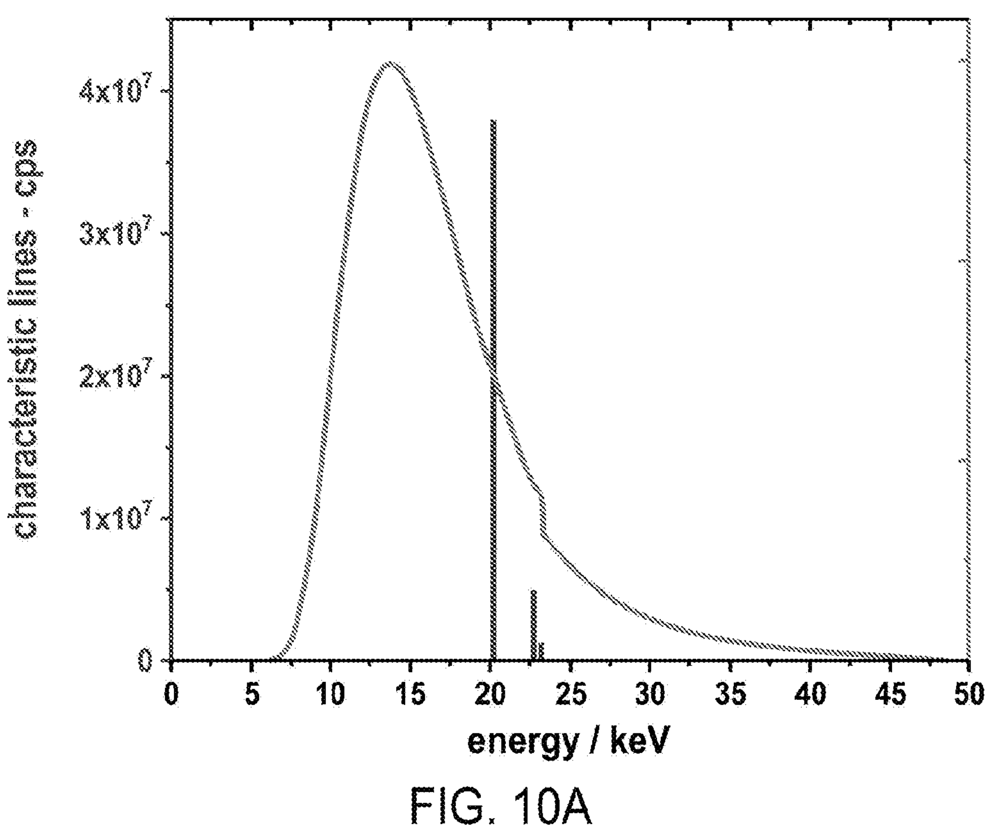
FIGS. 10A-10C are graphs showing tissue filter experiment.
Figure 10B:
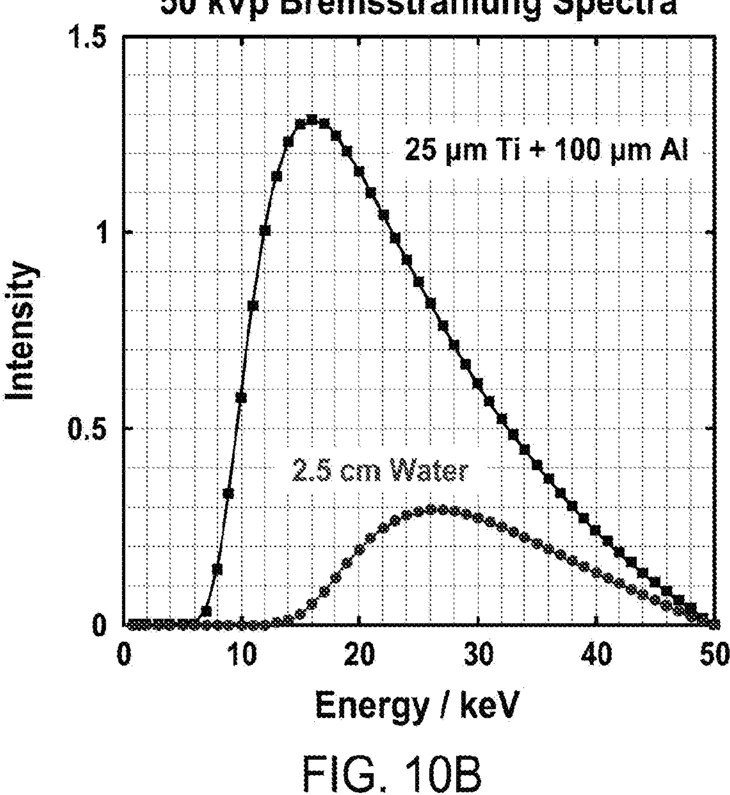
Figure 10C:
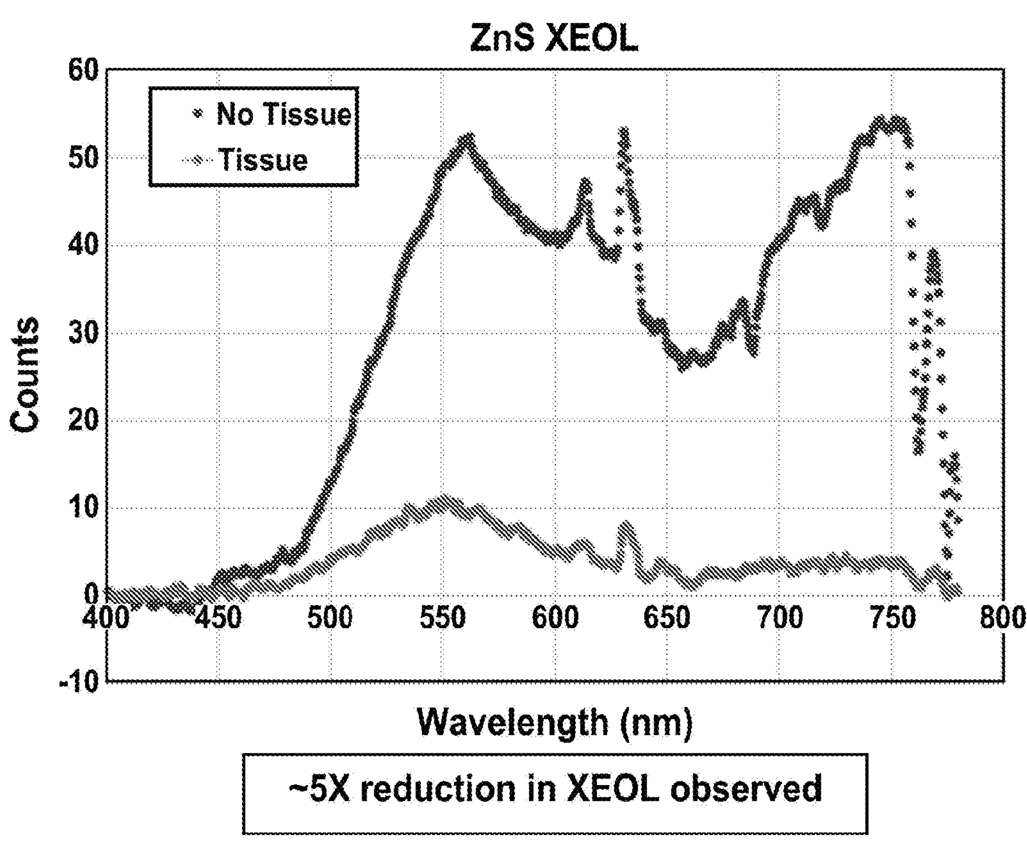

Tissue Filter Experiment: FIGS. 10A-10C are graphs showing a tissue filter experiment. FIG. 10A shows an x-ray Spectra (Bright XEOL detected @21keV (Elettra) but non-penetrating x-rays used) conducted on a Bruker XRF M1 Tool. FIG. 10B shows the calculated 50 kVp Bremsstrahlung spectra for this source with and without 2.5 cm of water to simulate tissue absorption in the body. FIG. 10C shows the observed XEOL of a ZnS film without (top) and with (bottom) a 2.5 cm thick tissue filter (lean beef). This data confirms the calculation in FIG. 10B that indicates a 5× reduction in XEOL is expected at 21 kVp when a 2.5 cm tissue slice is placed between the X-ray source and NPs.

NPs solution and sedimentation tests: Eu-doped HA and Eu-doped $SiO_2$ NPs were ground with a pestle and mortar and then dispersed in two different solutions:

1. (Eu—HA; Eu—$SiO_2$) Pure deionized water solution—NPs conc. 1 mg/ml 2. (Eu—HA; Eu—$SiO_2$) 0.3% water/BSA solution—NPs conc. 1 mg/ml ZGO:Cr—SiC NPs were dispersed in polyethylenimine PEI to form a third solution:

3. (ZGO:Cr—SiC) PEI solution—NPs conc. 1 mg/ml.

The solutions were sonicated in a water bath for 10-15 min at 12 W. For Eu-doped HA dispersed in 0.3% BSA—no sedimentation was observed within 24 h. NP average size distribution (next day) was about 270 nm and a polydispersion index PDI of 0.17 were determined. For Eu-doped HA dispersed in pure deionized water, the mixture re-precipitated after 1-2 hours. The Z-potential on the 1 mg/ml dispersion in BSA 0.3% was measured to be −27.3 mV. For Eu-doped $SiO_2$ dispersed in 0.3% BSA and in pure deionized water, no sedimentation was observed within 24 h for both solutions. The NP average size distribution (next day) was about 190 nm and a polydispersion index of 0.11 were determined. The Z-potential on the 1 mg/ml dispersion in BSA 0.3% shows a value of −28.6 mV and in pure DI water −12.5 mV. For ZGO:Cr-SiC NPs dispersed in PEI, no sedimentation process was observed within 24 h. The NP average size distribution (next day) was about 170 nm and a polydispersion index of 0.23 were determined. The Z-potential on the 1 mg/ml dispersion in PEI was measured to be +45.2 mV.

NP optical properties under x-ray irradiation: x-ray Excited Optical Luminescence (XEOL) measurements were performed at the ELETTRA synchrotron facility (Italy). The samples included solid powders and NP dispersed solutions. Photon flux at 21 keV was calculated to be $4.8\times10^{11}$ ph/s for powders; $6.4\times10^{11}$ ph/s for colloidal solution with a spot size of 1500 $\mu m^2$.

Figure 11A:
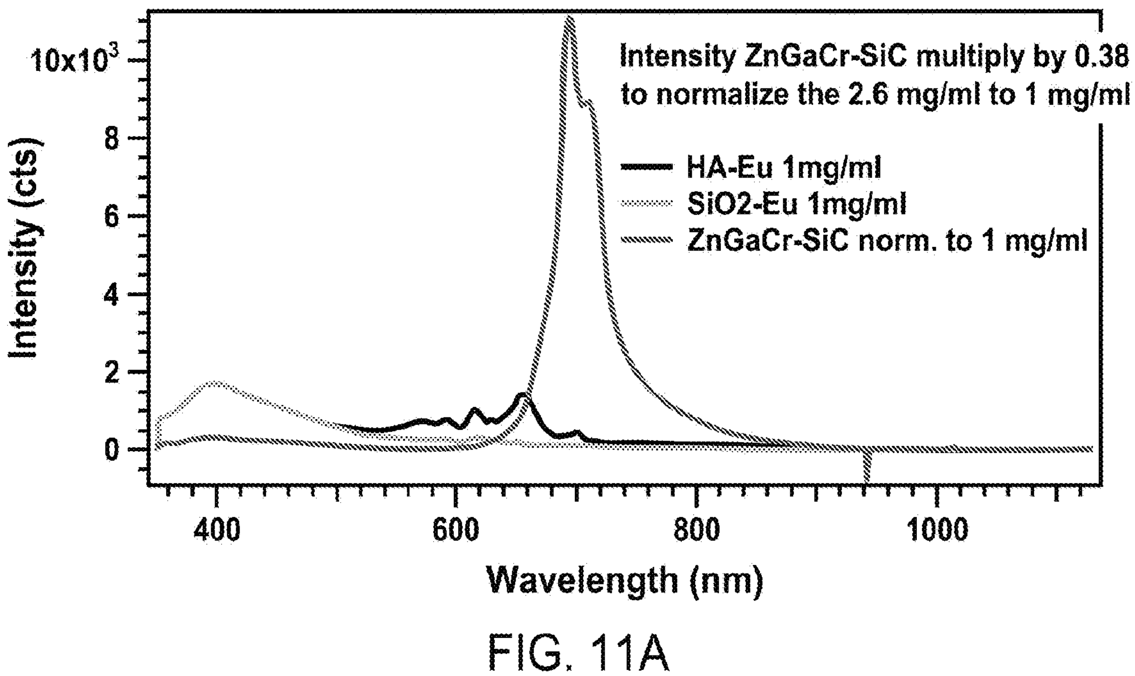
FIGS. 11A-11C are graphs showing emission of three types of NPs (HA-Eu, $SiO_2$—Eu, ZGO:Cr/SiC) in solution @1 mg/ml (FIG. 11A), in powder (FIG. 11B), and normalized @ 700 nm (FIG. 11C) under x-ray excitation at 21 KeV.
Figure 11B:
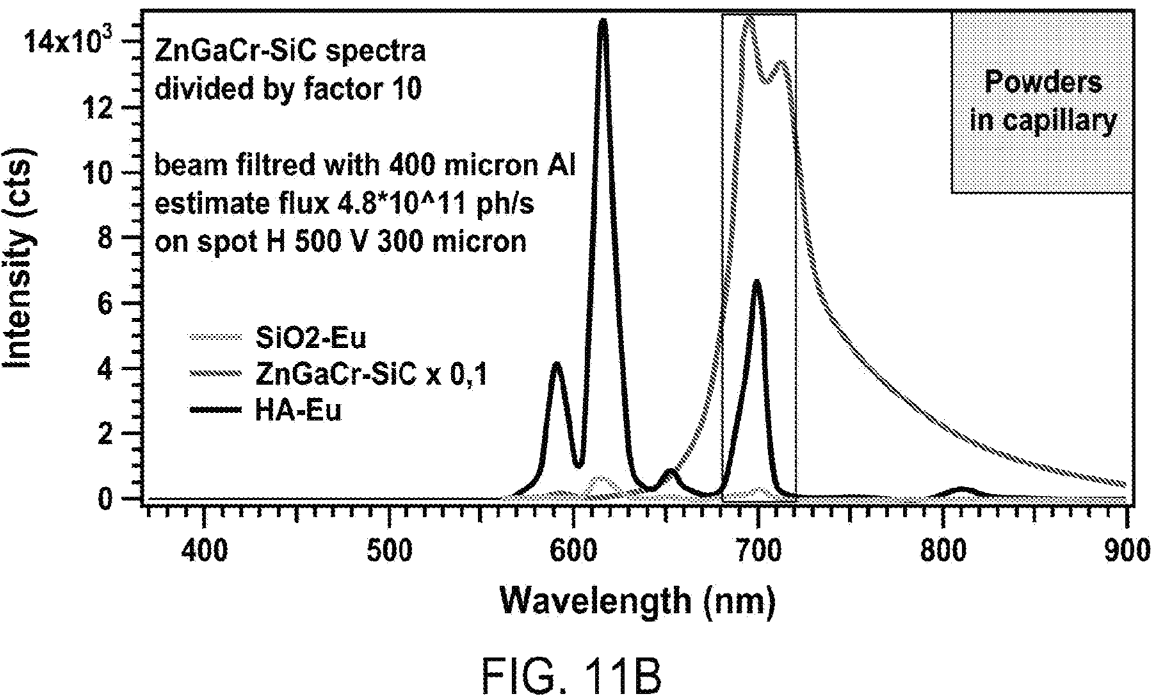
Figure 11C:
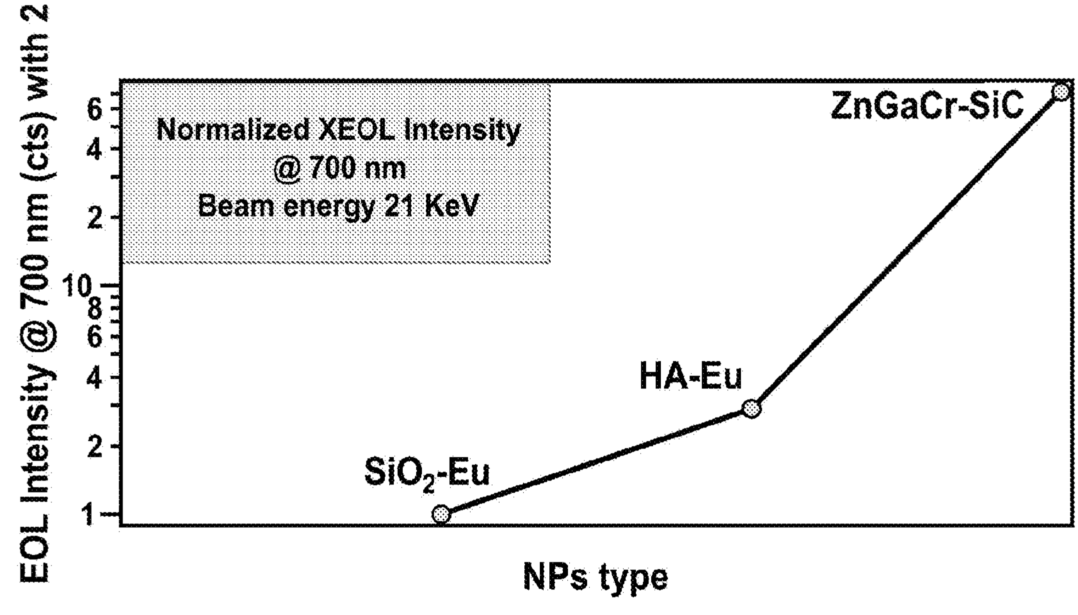

All three types of NPs (HA-Eu, Eu—$SiO_2$, ZGO:Cr—SiC) show emission at 700 nm under x-ray excitation at 21 KeV. FIGS. 11A-11C are graphs showing emission of NPs (HA-Eu, Eu—$SiO_2$, ZGO:Cr—SiC) in solution 1 mg/ml (FIG. 11A), in powder (FIG. 11B), and normalized @ 700 nm (FIG. 11C) under x-ray excitation at 21 keV. In the colloidal solution, the ZGO:Cr—SiC NPs emission is 23 times higher than that of HA-Eu NPs and 71 times higher than that of $SiO_2$—Eu NPs. Additional elements such as Au could be inserted in the HA-Eu and Eu—$SiO_2$ NPs to improve the x-ray stopping power and the NIR luminescence at 700 nm.

Figure 12A:
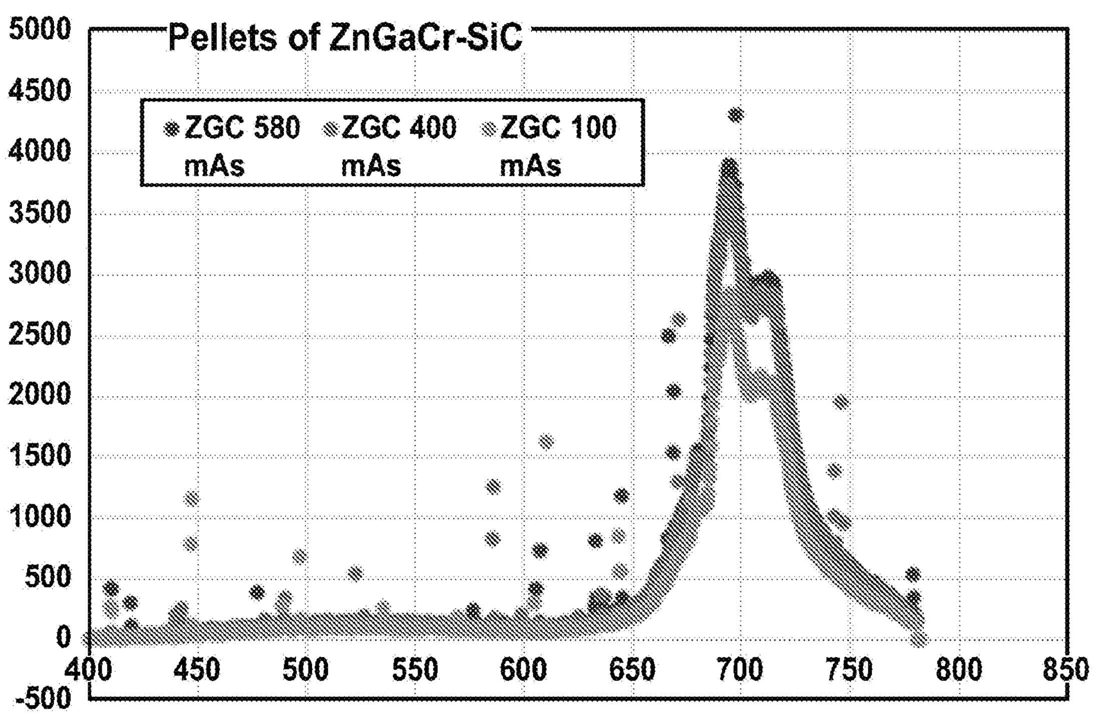
FIGS. 12A-12B are graphs showing XEOL of ZGO:Cr/SiC (FIG. 12A) and HA-Eu (FIG. 12B) pellets when illuminated with a standard radiology machine @100 kVp as a function of beam current-time (mAs).
Figure 12B:
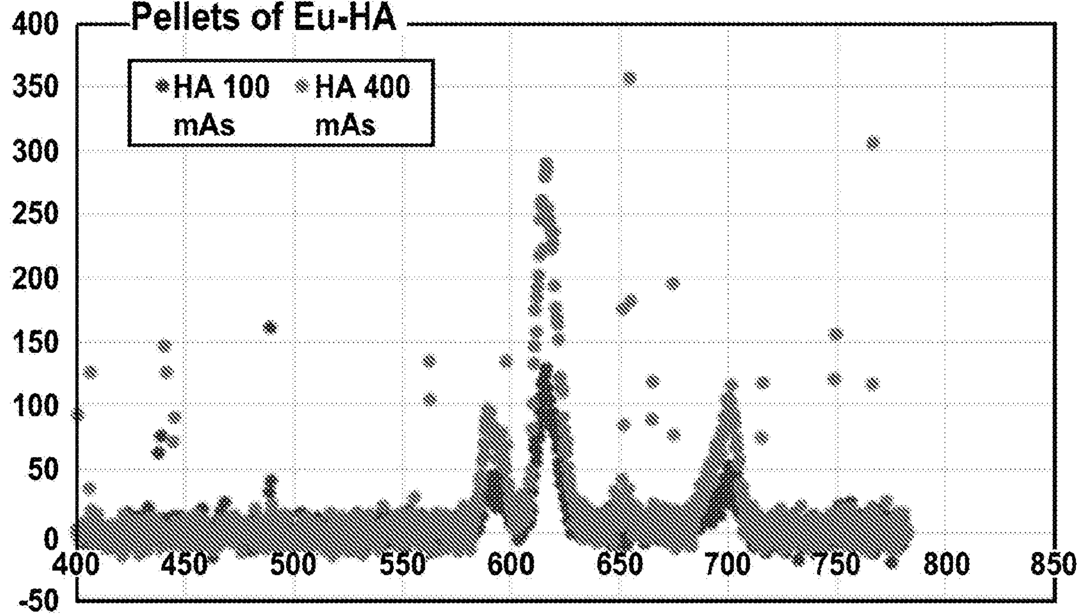

XEOL testing with standard radiology x-ray machine: Additional x-ray measurements were performed on the NPs with a standard radiology machine operating at 100 keV. The samples included pellets made from pressed NP powder and NPs dispersed in solution. Luminescence induced by x-rays provided by a standard radiology machine was detected from pellets formed from pressed ZGO:Cr—SiC and Eu—HA NPs. Only a very weak signal was detectable from the Eu—$SiO_2$ pellet. ZGO:Cr—SiC, Eu—HA and Eu—$SiO_2$ NP dispersions were tested but no outcoming luminescence was detectable, most probably due to sedimentation of the NPs on the bottom part of the capillary and the difficulty in aligning the optical fiber with the capillary used to hold the NPs in solution. FIGS. 12A-12B are graphs showing XEOL under x-ray excitation of ZGO:Cr-SiC (FIG. 12A) and Eu—HA (FIG. 12B) pellets provided by a standard radiology machine. X-ray flux at 100 kVp was approximately 2 orders of magnitude less than XRD1 @Elettra (21 kVp).

Summary: in this example, conversion of x-ray photons (energy) to near IR photons (energy) via XEOL has been demonstrated. Four (4) nanostructures have yielded NIR at ~700 nm: $SiO_x$:$Eu^{3+}$, HA:$Eu^{3+}$, ZGO:Cr-SiC and ZGO:Cr (not shown). X-ray dose at 100 kVp used is well below the tissue damage threshold and therefore the present methods can be used to only kill cancer cells. 2" slab of beef was used to show XEOL reduction @ ~20 keV—tissue transparent for x-ray energy >60 keV.

Publications cited herein are hereby specifically incorporated by reference in their entireties and at least for the material for which they are cited.

While it should be understood that while the present disclosure has been provided in detail with respect to certain illustrative and specific aspects thereof, it should not be considered limited to such, as numerous modifications are possible without departing from the broad spirit and scope of the present disclosure as defined in the appended claims. It is, therefore, intended that the appended claims cover all such equivalent variations as fall within the true spirit and scope of the invention.

What is claimed is:

1. A method for the treatment of a cancer in a subject in need thereof comprising:

(a) administering a therapeutically effective amount of a near-infrared antibody-photoabsorber conjugate (APC) to the subject, wherein upon administration the near-infrared APC is at least partially taken up into the cancer tissue and binds to a cell surface protein present within the cancer tissue;

(b) administering a therapeutically effective amount of an X-ray absorbing nanostructure (NS) to the subject, wherein the X-ray absorbing NS is at least partially taken up into the cancer tissue upon administration;

(c) exposing the cancer tissue to X-ray radiation, wherein upon exposure of the cancer tissue to the X-ray radiation, the X-ray absorbing NS absorbs the X-ray radiation and emits near-infrared (NIR) light; and wherein the X-ray absorbing nanostructure comprises silica ($SiO_2$), hydroxyapatite (HA), zinc-gallium-oxide (ZGO), silicon carbide (SiC), or a combination thereof, and is doped with a dopant selected from europium ($Eu^{3+}$), chromium ($Cr^{3+}$), gold (Au), other x-ray absorbing heavy element dopants, or a combination thereof; and wherein the dopant is present in an amount of from 0.01 to 10% by weight, based on the total weight of the X-ray absorbing nanostructure; and wherein the emitted near-infrared light has a peak wavelength between about 650 nm and about 750 nm that overlaps an absorption band of the APC and is emitted in an amount effective to induce cancer cell death at an X-ray dose of from about 0.1 Gy to about 2.0 Gy.

2. The method of claim 1, further comprising exposing the cancer tissue to near-infrared (NIR) light prior to step (b).

3. The method of claim 1, wherein the X-ray absorbing nanostructure comprises europium-doped $SiO_2$ nanoparticles (Eu—$SiO_2$), europium-doped hydroxyapatite nanoparticles (Eu—$HP_2$), chromium doped zinc-gallium-oxide (ZGO:Cr) nanoparticles, chromium-doped zinc-gallium-oxide shell with a SiC NP core (ZGO:Cr_SiC), SiC nanowire, SiC nanoparticle, or combinations thereof.

4. The method of claim 1, wherein the X-ray absorbing nanostructure is a core/shell nanowire or a core/shell nanoparticle, or a combination thereof.

5. The method of claim 1, wherein the X-ray absorbing nanostructure has a diameter from about 1 nm to about 350 nm.

6. The method of claim 1, wherein the X-ray absorbing nanostructure is functionalized with a surface-bound molecule.

7. The method of claim 6, wherein the surface bound molecule comprises a surfactant, a dispersant, a targeting agent which facilitates delivery of the nanoparticle to the cancer cell, or a combination thereof.

8. The method of claim 1, wherein the antibody-photoabsorber conjugate is an antibody-IR700 conjugate.

9. The method of claim 1, wherein the cell surface protein is selected from HER1, HER2, CD20, CD25, CD33, CD52, CEA, CA125, AFP, Lewis Y, TAG72, VEGF, PSMA, EGFR, PDGFRα, or a combination thereof.

10. The method of claim 1, wherein the antibody-photoabsorber conjugate is a cetuximab-IR700 conjugate, a panitumumab-IR700 conjugate, a trastuzumab-IR700 conjugate, a pertuzumab-IR700 conjugate, a capromab-photoabsorber conjugate, or a combination thereof.

11. The method of claim 1, wherein the cancer is a locally advanced solid tumor.

12. The method of claim 1, wherein the subject has a deep-tissue cancer, or cancer of the brain, lung, pancreas, stomach, colon, rectum, bladder, liver, spleen, ovaries, or a combination thereof.

13. The method of claim 1, wherein the subject is a human.

14. The method of claim 1, wherein the method further comprises administering an additional therapeutic agent.

15. A method for the treatment of a cancer in a subject in need thereof comprising:

(a) administering a therapeutically effective amount of a near-infrared antibody-photoabsorber conjugate (APC) to the subject, wherein upon administration the near-infrared APC is at least partially taken up into the cancer tissue and binds to a cell surface protein present within the cancer tissue;

(b) exposing the cancer tissue to near-infrared (NIR) light;

(c) administering a therapeutically effective amount of an X-ray absorbing nanostructure (NS) to the subject, wherein the X-ray absorbing NS is at least partially taken up into the cancer tissue upon administration; and (d) exposing the cancer tissue to X-ray radiation, wherein upon exposure of the cancer tissue to X-ray radiation, the X-ray absorbing NS absorbs the X-ray radiation and emits NIR light; and wherein the X-ray absorbing nanostructure comprises silica ($SiO_2$), hydroxyapatite (HA), zinc-gallium-oxide (ZGO), silicon carbide (SiC), or a combination thereof, and is doped with a dopant selected from europium ($Eu^{3+}$), chromium ($Cr^{3+}$), gold (Au), other x-ray absorbing heavy element dopants, or a combination thereof; and wherein the dopant is present in an amount of from 0.01 to 10% by weight, based on the total weight of the X-ray absorbing nanostructure; and wherein the emitted near-infrared light has a peak wavelength between about 650 nm and about 750 nm that overlaps an absorption band of the APC and is emitted in an amount effective to induce cancer cell death at an X-ray dose of from about 0.1 Gy to about 2.0 Gy.

* * * * *